US011627877B2

(12) United States Patent
Hanina et al.

(10) Patent No.: US 11,627,877 B2
(45) Date of Patent: Apr. 18, 2023

(54) APPARATUS AND METHOD FOR USER EVALUATION

(71) Applicant: AIC Innovations Group, Inc., New York, NY (US)

(72) Inventors: Adam Hanina, New York, NY (US); Ryan Bardsley, Manchester-by-the-Sea, MA (US); Michelle Marlborough, Red Hook, NY (US); Daniel Glasner, New York, NY (US); Dehua Lai, Elmhurst, NY (US); Xiaoguang Lu, West Windsor, NJ (US); Edward Ikeguchi, New York, NY (US)

(73) Assignee: AIC Innovations Group, Inc., New York, NY (US)

( * ) Notice: Subject to any disclaimer, the term of this patent is extended or adjusted under 35 U.S.C. 154(b) by 17 days.

(21) Appl. No.: 16/254,456

(22) Filed: Jan. 22, 2019

(65) Prior Publication Data
US 2019/0290129 A1 Sep. 26, 2019

Related U.S. Application Data

(60) Provisional application No. 62/721,456, filed on Aug. 22, 2018, provisional application No. 62/648,815, (Continued)

(51) Int. Cl.
A61B 5/00 (2006.01)
G16H 40/67 (2018.01)
(Continued)

(52) U.S. Cl.
CPC .......... A61B 5/0022 (2013.01); G06V 40/174 (2022.01); G16H 40/67 (2018.01); G16H 50/20 (2018.01); G16H 20/10 (2018.01)

(58) Field of Classification Search
CPC ..... A61B 5/0022; A61B 5/4803; A61B 5/165; A61B 5/6898; A61B 5/7246;
(Continued)

(56) References Cited

U.S. PATENT DOCUMENTS 5,774,591 A 6/1998 Black
5,802,220 A 9/1998 Black
(Continued)

FOREIGN PATENT DOCUMENTS

CN 2667828 6/2008
WO WO 2015/191805 12/2015
WO WO 2017/177235 10/2017

OTHER PUBLICATIONS

Digital Health Summit [online], "Live Demo Artificial Intelligence—Infinite Possibilities (AiCure) @ Digital Health Summit CES 2017," posted Jan. 14, 2017, <https://www.youtube.com/watch?v=XhaWv66o2Z8>, 1 page [Video Submission].
(Continued)

Primary Examiner — Christopher A Flory
(74) Attorney, Agent, or Firm — Fish & Richardson P.C.

(57) ABSTRACT

A method includes providing one or more instructions to perform a first action associated with administration of a medication; obtaining first data representing a capture of a patient performing the first action based on the one or more instructions; extracting information about movements of the patient from the first data; presenting an image configured to induce an emotional response in the patient; obtaining second data representing capture of the patient performing one or more microexpressions within 250 milliseconds of presentation of the image; obtaining additional data including one or more of demographic information of the patient, information of a disease associated with the patient, or one or more characteristics of the medication; and based on the extracted information about the movements, the one or more
(Continued)

microexpressions, and the additional data, determining a medical outcome including a progression of the disease in the patient.

23 Claims, 17 Drawing Sheets

Related U.S. Application Data filed on Mar. 27, 2018, provisional application No. 62/645,671, filed on Mar. 20, 2018.

(51) Int. Cl.
 *G16H 50/20* (2018.01)
 *G06V 40/16* (2022.01)
 *G16H 20/10* (2018.01)

(58) Field of Classification Search
 CPC ... A61B 5/4839; A61B 5/7275; A61B 5/1128; G16H 50/20; G16H 20/10; G16H 40/67; G06V 40/174
 See application file for complete search history.

(56) References Cited

U.S. PATENT DOCUMENTS

| | | | |
|---|---|---|---|
| 7,593,952 B2 * | 9/2009 | Soil | G16H 70/60 707/999.102 |
| 7,853,456 B2 * | 12/2010 | Soto | G06Q 40/08 703/2 |
| 8,666,781 B2 | 3/2014 | Hanina et al. | |
| 8,731,961 B2 | 5/2014 | Hanina et al. | |
| 8,781,856 B2 | 7/2014 | Hanina et al. | |
| 9,183,601 B2 | 11/2015 | Hanina et al. | |
| 9,256,776 B2 | 2/2016 | Hanina et al. | |
| 9,293,060 B2 | 3/2016 | Hanina et al. | |
| 10,264,971 B1 | 4/2019 | Kennedy et al. | |
| 2003/0118974 A1 | 6/2003 | Obrador | |
| 2008/0140444 A1 | 6/2008 | Karkanias | |
| 2008/0294012 A1 | 11/2008 | Kurtz et al. | |
| 2009/0093685 A1 | 4/2009 | Vu et al. | |
| 2010/0172567 A1 | 7/2010 | Prokoski | |
| 2011/0119073 A1 | 5/2011 | Hanina et al. | |
| 2011/0153360 A1 * | 6/2011 | Hanina | G16H 20/10 705/3 |
| 2012/0009555 A1 | 1/2012 | Hanina et al. | |
| 2012/0243751 A1 | 9/2012 | Zheng | |
| 2012/0316897 A1 | 12/2012 | Hanina et al. | |
| 2013/0063579 A1 | 3/2013 | Hanina et al. | |
| 2013/0085808 A1 | 4/2013 | Forbes | |
| 2013/0169781 A1 | 7/2013 | Hanina | |
| 2013/0173287 A1 * | 7/2013 | Cashman | H04N 7/141 705/2 |
| 2014/0016860 A1 | 1/2014 | Senechal et al. | |
| 2014/0052475 A1 * | 2/2014 | Madan | G16H 50/30 705/3 |
| 2014/0113263 A1 * | 4/2014 | Jarrell | G09B 23/28 434/262 |
| 2014/0153794 A1 * | 6/2014 | Varaklis | A61B 5/1124 382/128 |
| 2014/0315168 A1 | 10/2014 | Movellan et al. | |
| 2014/0316881 A1 | 10/2014 | Movellan et al. | |
| 2016/0034764 A1 | 2/2016 | Connor | |
| 2016/0354039 A1 | 12/2016 | Soto et al. | |
| 2017/0032092 A1 * | 2/2017 | Mink | G06Q 10/1095 |
| 2017/0071531 A1 | 3/2017 | Ehrhart et al. | |
| 2017/0238860 A1 | 8/2017 | El Kaliouby | |
| 2017/0323485 A1 * | 11/2017 | Samec | G02B 27/0172 |
| 2017/0364741 A1 | 12/2017 | Hau | |
| 2018/0366225 A1 * | 12/2018 | Mansi | G16H 50/20 |
| 2019/0110754 A1 | 4/2019 | Rao et al. | |
| 2019/0239791 A1 * | 8/2019 | Beck | A61B 3/112 |
| 2019/0290127 A1 | 9/2019 | Hanina et al. | |
| 2019/0290128 A1 | 9/2019 | Hanina et al. | |

OTHER PUBLICATIONS

PCT International Preliminary Report on Patentability in International Appln. No. PCT/US2019/021913, dated Sep. 22, 2020, 12 pages.

EP Extended European Search Report in European Appln. No. 19772546.8, dated Apr. 1, 2021, 8 pages.

Stuart [online], "Founder's Story: Adam Hanina, CEO & Co-Founder, AiCure," Presented at the Cornell Health Tech Conference, Mar. 4, 2016, posted Apr. 5, 2016, retrieved on Feb. 9, 2021, <https://www.youtube.com/watch?v=Cm3MtgsKbrM>, 1 page [Video Submission].

U.S. Appl. No. 61/467,209, Zheng et al., Baseline Face Analysis, filed Mar. 24, 2011, 13 pages.

Intentalionai Search Report and Written Opinion for International Appln. No. PCT/US2019/021913, dated May 30, 2019, 13 pages.

* cited by examiner

FIG. 6

| | | |
|---|---|---|
| Longitudinal | Baseline Shift Analysis 910 | |
| Content | NLP Content Analysis 920 | |
| Speech patterns | Prosodic Analysis 930 | |
| Physical | Gross movement 940 | Illustrators 945 | Manipulators 950 |
| Affect | Microexpressions 955 | Expressions 960 | Attitudes 965 |
| Time | Temporal Analysis 970 | |

- Time to first AU shift
- Time to vocal response
- Duration of response

- Quantification of pauses
- Prompt interaction analysis
- Time to interaction with manual navigation

FIG. 9

APPARATUS AND METHOD FOR USER EVALUATION

CROSS-REFERENCE TO RELATED APPLICATIONS

This application claims the benefit of U.S. Provisional Patent Application Ser. No. 62/721,456 filed Aug. 22, 2018 to Hanina et al. titled "Apparatus and Method for User Evaluation; U.S. Provisional Patent Application Ser. No. 62/648,815 filed Mar. 27, 2018 to Hanina et al. titled "Apparatus and Method for Computational Diagnosis of a User; and U.S. Provisional Patent Application Ser. No. 62/645,671 filed Mar. 20, 2018 to Hanina et al. titled "Apparatus and Method for Interacting with a User", the entire contents of each of these applications being incorporated by reference herein.

FIELD

This disclosure relates generally to the application of one or more novel monitoring systems, including one or more of visual monitoring, audio monitoring, or other sensor data monitoring of one or more characteristics of a user, and more particularly, to the correlation of results of these unique measurements to quantify changes in the health or other status of the user, and to further allow for prediction of future response to the application of a drug, other therapy, or any change in conditions. The disclosure further relates to a system capturing the collected and correlated information, analyzing that information to determine further correlations, and allowing a user to provide input querying the stored data in order to provide information related to the applicability of a particular medication to a potential patient, or a type of medication to investigate in order to address a particular patient or disease.

BACKGROUND

When evaluating a medical patient, doctors or other healthcare providers perform a generally manual process. This process includes reviewing current characteristics of the patient against a predetermined set of standards to determine any deviation from those standards. So, the healthcare provider may take the temperature or blood pressure of the patient, and compare to standard, acceptable ranges for each such measurement. By running through a sequence of these comparisons, a battery of tests may be performed to evaluate the health of the patient. Similarly, neurological or psychiatric tests may be applied that request the patient respond to specific questions or tasks, so that the responses to these questions can be used to determine a disease state of a patient, for example.

For more complex evaluations, more robust sets of tests may be administered, including a series of tests that together may provide insight as to the health of the patient. If a patient is being evaluated for a blood illness, for example, a sequence of blood tests may be employed, while if the patient is being evaluated for a mental health issue, such testing may comprise a sequence of questions that have been validated to allow for confirmation of a diagnosis of a patient. Both methods of surveying the patient's current condition compare data collected to an accepted range for what is considered "normal."

SUMMARY

In U.S. patent application Ser. No. 12/620,686, filed Nov. 18, 2009, titled Method and Apparatus for Verification of Medication Administration Adherence, abandoned; U.S. patent application Ser. No. 13/558,377, filed Jul. 26, 2012, titled Method and Apparatus or Verification of Medication Administration Adherence, now U.S. Pat. No. 8,781,856; U.S. patent application Ser. No. 12/646,383, filed Dec. 23, 2009, titled Method and Apparatus for Verification of Clinical Trial Adherence, abandoned; U.S. patent application Ser. No. 13/558,380, filed Jul. 26, 2012, titled Method and Apparatus for Verification of Clinical Trial Adherence, now U.S. Pat. No. 8,731,961; U.S. patent application Ser. No. 12/646,603, filed Dec. 23, 2009, titled Method and Apparatus for Management of Clinical Trials, Now U.S. Pat. No. 8,666,781; U.S. patent application Ser. No. 12/728,721, filed Mar. 22, 2010, titled Apparatus and Method for Collection of Protocol Adherence Data, now U.S. Pat. No. 9,183,601; U.S. patent application Ser. No. 12/815,037, filed Jun. 14, 2010, titled Apparatus and Method for Recognition of Patient Activities when Obtaining Protocol Adherence Data, now U.S. Pat. No. 9,293,060; U.S. patent application Ser. No. 13/189,518, filed Jul. 24, 2011, titled Method and Apparatus for Monitoring Medication Adherence, currently pending; U.S. patent application Ser. No. 13/235,387, filed Sep. 18, 2011, titled Apparatus and Method for Recognition of Patient Activities, currently pending; U.S. patent application Ser. No. 13/674,209, filed Nov. 12, 2012, titled Method and Apparatus for Identification, now U.S. Pat. No. 9,256,776; and U.S. patent application Ser. No. 13/674,459, filed Nov. 12, 2012, titled Method and Apparatus for Recognition of Inhaler Actuation, currently pending; the contents of these applications being incorporated herein by reference, the present disclosure is directed to systems, methods and apparatuses that allow for complete control and verification of adherence to a prescribed medication protocol or machine or apparatus use in a clinical trial or disease management setting, whether in a health care provider's care, or when self-administered in a homecare situation by a patient.

The application of the testing batteries, as discussed above, takes significant healthcare provider time, is subject to variability in accordance with subjectivity in grading responses across different healthcare providers and may also be difficult to administer outside of a doctor's office or medical clinic. Furthermore, the amount and complexity of information that is used in making such determinations may not be processed individually by a human being. It is this rich set of historical information, collected concurrent information (for example, related to microexpressions that are not independently perceivable by a human) and other information collected and processed by the system that allow for the system of the present disclosure to provide results and analysis that are far more in depth, robust, consistent, and free of subjective bias when compared with those achievable by a human operator. Therefore, it would be beneficial to provide an improved process that overcomes these drawbacks of the prior art. The present disclosure is direction to, among other things, a system for collecting information from a large number of patients, processing this information to allow for a determination of correlations between collected data and changes in symptoms or other characteristics of the patients, to allow for observation of changes in future patients in order to then correlate with progression of disease. Furthermore, by additionally correlating medication adherence with those same changes in symptoms, it is possible to then predict responses to changes in symptoms by future patients in response to administration of particular medications. Additionally, by determining elements of the medication and correlating these elements similarly with changes in symptoms, not only the complete medications, but also aspects of the medication can be used to predict future responses to other medications (potentially new medication under development, by way of example) by different demographic groups of patients. Finally, by selecting particular symptoms or aspects of disease to be cured, medication combinations can be determined and perhaps generated that have the most likelihood of success.

In addition, this disclosure proposes a method for establishing a personalized medical baseline from which to compare shifts from any collected data. Furthermore, the present disclosure covers techniques for monitoring changes in a number of physical and other characteristics that are not visible to a human reviewer over time, and therefore requires the aid of an artificial intelligence system so that managing patient symptom changes as a holistic group of characteristics that may be correlated to changes in a disease being monitored.

Therefore, in accordance with the present disclosure, a novel system for tracking progression of symptoms of a patient is provided. Through baseline normalization, the use of both passive monitoring during medication adherence monitoring, and active monitoring during presentation of material to the patient, the systems and techniques disclosed herein are able to precisely monitor the patient and changes to symptoms or other identifying elements associated with the patient. These preferably lead to the ability to perform a differential analysis against healthy population and longitudinal self-comparison.

In some embodiments, the system therefore performs the following: 1) creating a patient-specific phenotype of the patient (for example, how severe a condition experienced by the patient is in context to all the other patients who have gone through the system); 2) determining a rate of decline or progression of the symptoms/disease for the particular patient; 3) generating a calibration point for a specific medication based on effectiveness to impact that specific indication in an objective manner; and 4) creating a scoring system to show effectiveness and safety of a medication in comparison to predecessor drugs or other treatment options that have gone through the system.

In accordance with another aspect of the present disclosure, data collected across multiple patients or users may be compiled to allow for further analysis. In addition to determining a user baseline, and averages of changes over time for patients in a particular population, the collected information may be used to determine potential outcomes of other medications along similar dimensions. Such dimensions may include ability to reduce obesity, reduce suicidal thoughts, improve cognition, reduce pain, improve concentration, changes in tremor, or any other number of changes that may be determined. Thus, in accordance with another aspect of the present disclosure, the collected information is preferably analyzed along a plurality of dimensions so that expected changes along each of those dimensions may be predetermined. Each patient can also be characterized along one or more of these dimensions. Other aspects of the demographic information for each of the patients may provide the ability to then recognize characteristic changes along each of those dimensions categorized by demographic of the patient. Thus, by collecting information across all patients, categorizing the data by demographic, and analyzing the categorized data, predictions of future expected responses across these same dimensions can be determined.

In a still further aspect of the present disclosure, by also categorizing responses to the administration of medication along these dimensions by different of the demographic groups and determining aspects of medication responsible for changes to the characteristics along these same dimensions, it is then possible to determine potential future expectations of medication responsiveness based upon patient demographics, along these same dimensions. By searching a desired combination of results, the tool can be used as a medication identification tool, providing a guide for medications to be used to combat certain of the symptoms matching the dimensions.

Still other objects and advantages of the invention will in part be obvious and will in part be apparent from the specification and drawings.

In general, in some aspects, the subject matter of the present disclosure is directed to techniques comprising several steps and the relation of one or more of such steps with respect to each of the others, and an apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which:

FIG. 6 is a representation of an exemplary facial action coding system;

FIG. 9 depicts an exemplary analysis hierarchy;

DETAILED DESCRIPTION

Figure 1:
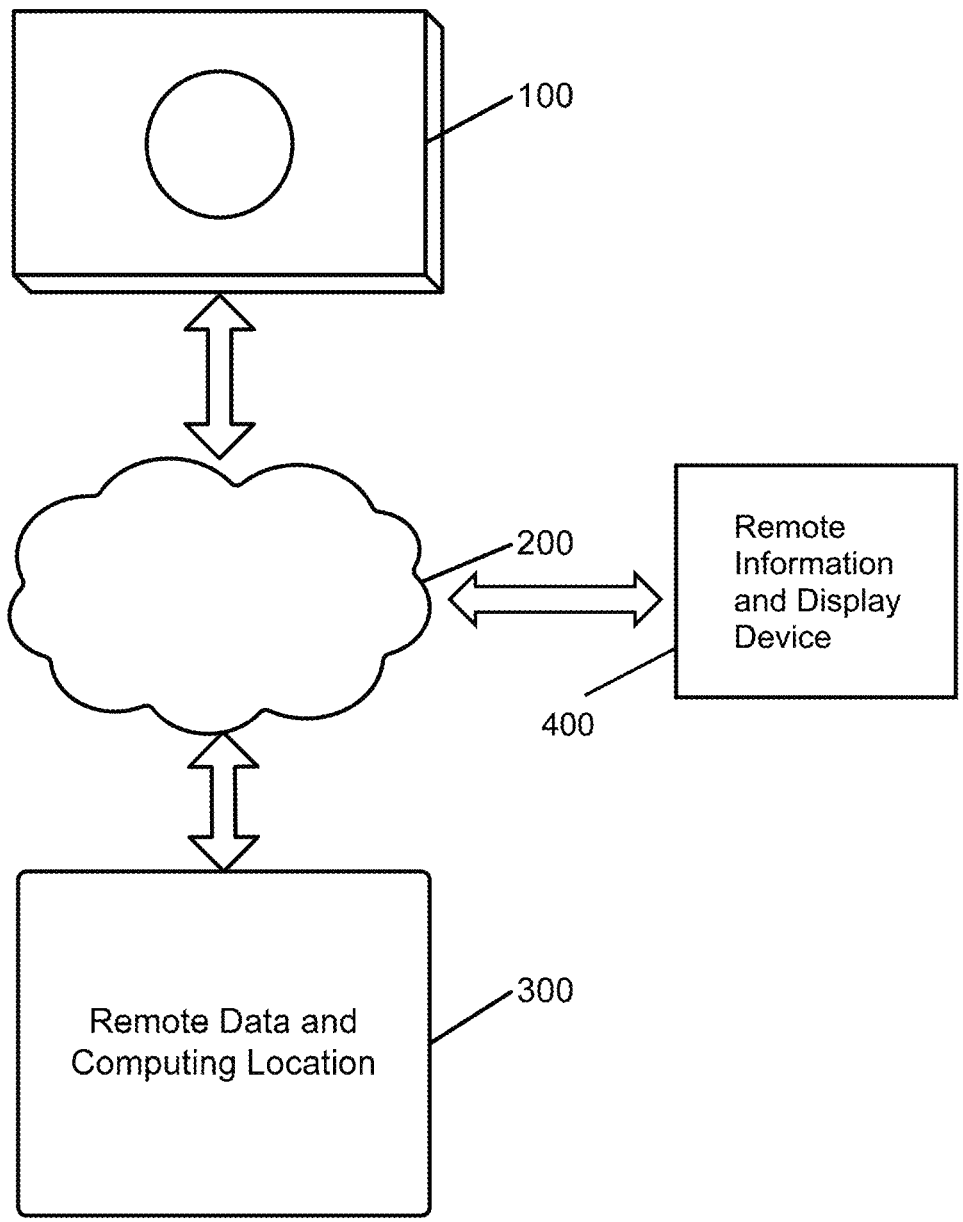
FIG. 1 depicts an exemplary data capture and transfer system.

A novel system for tracking progression of symptoms of a patient is provided in accordance with one or more embodiments of the present disclosure. The use of both passive monitoring during medication adherence monitoring, and active monitoring during presentation of material to the patient may be used to determine an individual baseline for a patient, and therefore the techniques disclosed herein enable precise monitoring of the patient and changes to symptoms or other identifying elements associated with the patient. These preferably lead to the ability to perform a differential analysis against healthy population and longitudinal self-comparison, and to determine progression of disease for a patient in relation to others in the same patient population, and also against the patient's own particular customized profile.

In general, in some aspects, the subject matter of the present disclosure recognizes the desire to be able to apply the above described system, and the audio/video information captured by the system, to perform unique healthcare evaluations. These evaluations are preferably based upon visual and other captured data that allows for an ongoing analysis of patient behavior, and the ability to monitor changes in symptoms of a patient employing visual and other observation, and to confirm a particular medical diagnosis, or changes in that diagnosis over time. Monitoring of such changes may be visually and otherwise confirmed based upon monitoring of a patient performance of one or more standard activities, such as while using the above medication monitoring system to monitor proper medication administration, or during another action typically asked of a patient ("passive monitoring"). These additional passive monitoring actions may include speaking with a healthcare provider, walking in a normal manner, holding a mobile device, taking a picture with a mobile device, speaking to a friend on a mobile device, typing a message on a mobile device, time in answering a call on a mobile device, responding to an instruction, and the like. These may include any normal action to be performed by a user, and the monitoring of one or more aspects of the user while performing the action. By employing a visual solution, this passive monitoring may be performed without the use of any additional hardware such as a wearable sensor, and therefore can be conducted in a far more unobtrusive manner.

Alternatively, the system may ask the patient to perform a particular set of actions in response to a displayed or otherwise presented stimulus. Thus, the patient may be shown one or more images, presented with one or more sounds, asked to respond to one or more questions, etc. that are specifically provided in order to test or record a particular response to the presented material. As opposed to passive monitoring, such active monitoring, while more intrusive, is able to be more particularly tailored to gather desirable information from a user as the collected information is not limited as in the passive monitoring situation. These questions may be provided in a flexible manner, dictated by prior response to the same or other questions by the patient, or may alternatively be based upon a standard set of questions typically presented to a particular patient population. While the content may be presented in a flexible manner, the method of data capture (audio, video, temporal, etc.) is preferably highly-specific and provides the context necessary to extract meaningful signals. The system may also perform multi-modal tests, thus allowing for monitoring of other action or characteristics of a patient while making the primary measurements using the audio/visual active or passive monitoring techniques.

Furthermore, in either scenario, baselines for the main components (speech, visual, gestural, and temporal) measures may be established, and then subsequent questioning may be determined based upon baseline results. For example, based upon the results received at baseline, a particular set of questions may be asked of the patient going forward. This method of "customizing" the question sets allows for the ability to best track changes in patient symptoms, while reducing the burden on the patient as much as possible. Not only may the question set be customized, but the precise mechanism for recognizing responses may also be customized based upon baseline or subsequent responses provided by the patient. For example, if a particular patient is determined to have symptoms or a disease that may result in an increased tremor in their hands, more attention to the hands may be provided in order to better differentiate between changes in the tremor. Similarly, if a patient is determined to have symptoms that may inhibit the ability to swallow a medication pill, extra attention may be provided to the throat of the patient, looking at swallowing micro movements, to better confirm pill swallowing.

Such processing may be employed across any measured parameter, and allows for significant customization of the system to not only different patient populations, but also to individual patients while reducing the potential processing burden on the system.

Visual Myography—An advantage of the present system is that by capturing and analyzing the frames of video of a person's face directly after the person is subjected to an event, such as viewing a provocative image or being asked a personal question, the system can quantify a person's unique myographic signature in response to that stimulus. For example, it has been discovered with the present systems that, in some embodiments, persons with negative symptoms of schizophrenia may elicit smaller changes in facial expression when shown both positive and negative imagery as compared with a healthy population. Additionally, when asked to describe the imagery and how it makes them feel, schizophrenics will offer less vocal response with distinct prosodic features than from healthy patients. By basing the patient's visual myographic signature on a comparison to their own, personally indexed visual baseline (established from a composite array of neutral expression imagery collected from the daily dosing application), the system can better extract variation from normal for that particular patient. In one embodiment, when five images are viewed weekly over the course of three months, persons with negative symptoms from schizophrenia will show a marked increase in both expression and prosody if the medication is effective in treating this type of ailment, which will help to separate placebo from drug effect in a clinical trial. Of course, other numbers of images or length of time may also be included.

Automated Negative Symptom Assessment—It has further been determined with the present systems that by recording audio and video of a person while the system asks them a set of questions, persons with negative symptoms of schizophrenia will elicit smaller changes in facial expression when they answer. Additionally, schizophrenics with negative symptoms will offer less vocal response with distinct prosodic features than from healthy patients. When a battery of questions is asked over the course of three months, persons with negative symptoms from schizophrenia will show a marked increase in both expression and prosody if a medication they are being provided is properly working.

The systems encompassed by the present disclosure may be configured to monitor video and audio in response to stimulus presented to the patient on a mobile or other electronic device, and further may monitor the patient's response employing other sensors, such as accelerometers, or the like associated with the mobile device. In some implementations, unique testing is performed in order to elicit the desired responses, employing visual recognition and analysis of facial expressions, audio analysis of changes in vocal characteristics, and recognition of other sensor input. These tests are performed at predetermined or flexible intervals, and therefore provide a unique picture of symptom progression of the patient in a manner not previously available.

Stimuli may be provided to the patient through conduct of an automated interview, when real time analysis of responses provided by the patient will influence the progress of the automated interview, and may also in part dictate the measurements and analysis to be performed by the system on the patient. Through unique branching logic that relies upon results from the real time analysis of patient responses, rather than simply a provided answer, more efficient and accurate monitoring and analysis may be provided. Branching not only considers the answers provided, but also, for example, the amount of time to respond, any delays in speech, the inflection of the voice of the user, measurements of levels of excitement or lack thereof, or any other number of non-traditional branching logic indicators, thus allowing for branching in response to perhaps a holistic view of the user, rather than simply their answer to the prior question. This flexibility allows for the system to continue such an interview in a more conversational manner, keeping the patient more comfortable while maximizing the amount of relevant information extracted from the interview systems. Additionally, such an automated system removes bias that may be introduced by a human interviewer, or because of inter-interviewer and intra-interviewer differences in presentation or evaluation criteria. Accordingly, the presently disclosed unique systems provide objective and repeatable benefits. The result is a customized interactive experience for the user with objective and quantifiable measurements. In one or more embodiments, the systems of the present disclosure may employ a data-driven machine learning based approach for modeling (feature extraction, selection, decision making, etc.) in order to analyze collected data, including visual data. For example, techniques may be used to model healthy population, and extract and select signature differential features in accordance with different artificial intelligence models.

In some embodiments, monitored characteristics also are used to assist in confirming medication administration. Thus, combined with direct monitoring of medication adherence, the further monitoring of physical and other characteristic that are expected to change in a known manner upon administration allows for an indirect, supportive confirmation of proper medication administration.

Figure 16:
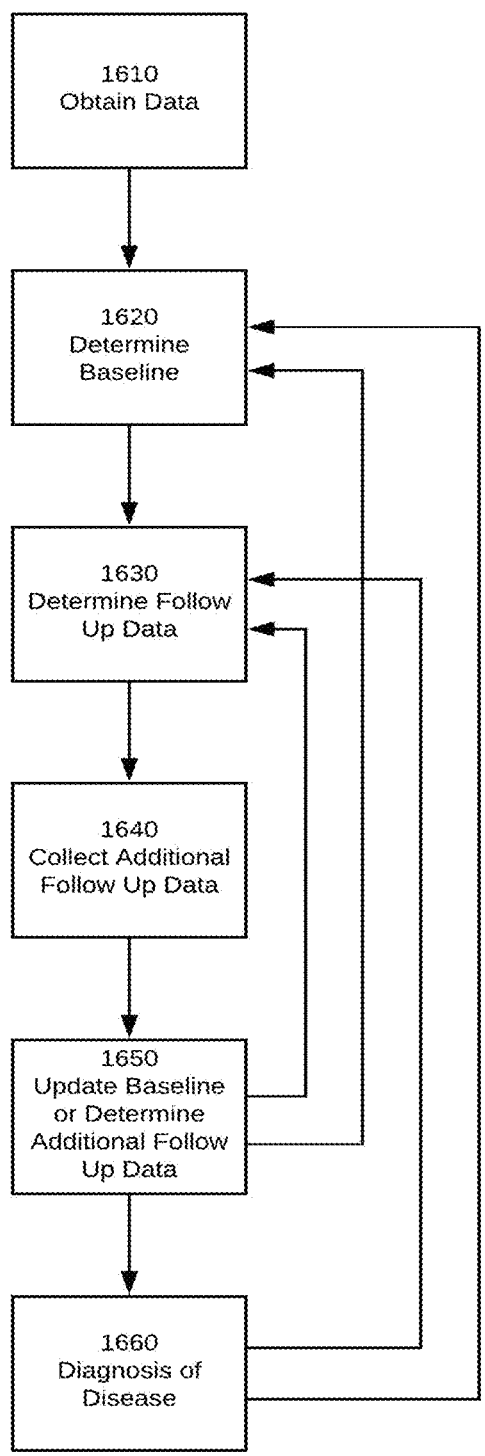
FIG. 16 is a flowchart diagram depicting an exemplary process for collecting and analyzing data collected.

As is therefore shown in FIG. 16, an exemplary process according to the present disclosure is shown. One or more of the steps of the process may be performed by the data capture and transfer system described in detailed below with reference to FIG. 1 and FIG. 2. The process includes, as step 1610 first obtaining data related to one or more physical or other attributes of a user, and may include audio and/or video data, vital signs, weight, or other physical attributes, responses to one or more presented inquiries or the like. This data may be collected, e.g., through microphones and cameras associated with a mobile device of a user. Upon collection of this information, processing then passes to step 1620 where a baseline for a particular user is determined in accordance with the collected information. Once this baseline for one or more of the collected data types is determined, processing passes to step 1630 where, based upon the baseline determination, one or more types of follow up information are determined to be collected. The follow up information may include, e.g., one or more passive or active presentation and collection of data, as will be described below, and may include collection of such data in accordance with other activities to be performed (such as medication administration, "passive") or in accordance with specific tasks presented to the user, preferably by display and speaker of the mobile device of the user ("active"). In some implementations, branching logic is employed in order to determine the follow up activities and information to be collected. Thus, baseline information may be employed to determine a possible disease or ailment of the user, and then more detailed information may preferably be determined useful to further evaluation any such condition. At step 1640 this additional follow up information is collected, and at step 1650 this additionally collected follow up information is employed to update the base line collected information (returning to step 1620), and may further be used to determine if any still additional branching logic is appropriate to identify even further desirable follow up information should be collected (returning to step 1630). Finally, at step 1660 a diagnosis or progression of disease is determined based upon changes in one or more of the collected information. Any such updated diagnosis may similarly be used to modify baseline at step 1620, or further information to be collected in accordance with branching logic at step 1630. After such diagnosis is determined to be complete, processing may end.

Figure 17:
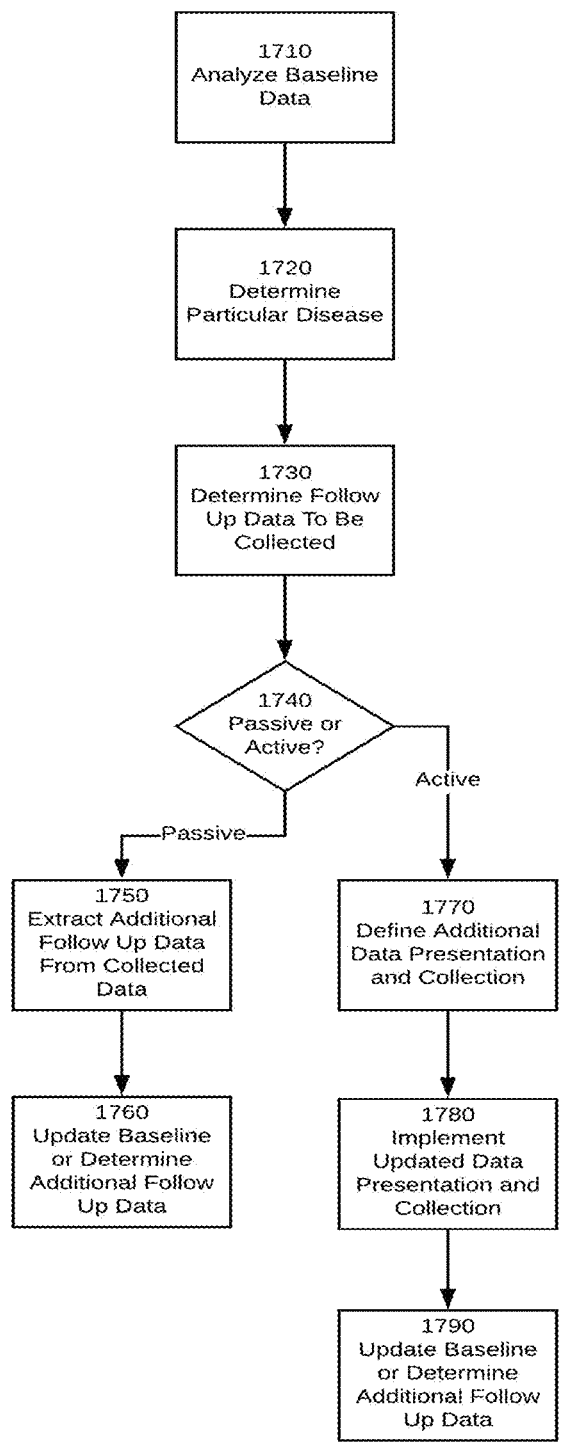
FIG. 17 is a flowchart diagram depicting an exemplary process for determining one or more follow up information to be collected.

Referring next to FIG. 17, an example process for determining one or more follow up information to be collected, as described in step 1630 of FIG. 16, is depicted. One or more of the steps of the process may be performed by the data capture and transfer system described in detailed below with reference to FIG. 1 and FIG. 2. As is shown in FIG. 17, processing begins at step 1710 where baseline information is analyzed to determine whether portions of the baseline information are indicative of a particular disease of interest, or even whether a particular symptom is appropriate to be further monitored. At step 1730 branching logic is preferably employed in order to determine whether follow up information is to be collected. Then at step 1740 it is queried whether data is being collected in an active or passive manner. In some implementations, this can be important given that data collection techniques may dictate changes to the processing that is employed. By way of example, if a passive data collection technique is to be employed, processing passes to step 1750 where the updated data extraction technique includes changes in the analysis techniques employed on the passive data that is collected. Because the data is collected passively, the data collection process and stimuli cannot be altered, and updated data extraction is the only possibly-employed process. Thus, while alternative data analysis can certainly be employed, the monitoring process cannot be altered (i.e. by presenting a different image or instruction to a user) because of the passive nature of the data collection. It may be possible, however, to add means of data capture in response to passively collected information. For example, if video capture is employed, and it is observed that the mouth of a user may be moving, audio may selectively also be employed. Thus, while branching logic may be more actively employed in active situations, there is possibility for branching of the logic in passive situation as well, but not to the extent to adjusting stimuli presented to the user. Once determined, processing passes to step 1760, representative of step 1650 of FIG. 16, where baseline data is updated in accordance with this updated analysis.

If, on the other hand, it is determined at step 1740 that data collection is active, processing passes to step 1770 and one or more updated data presentation and collection techniques are defined. Thus, new scales or other presentations of data and collection of responses are defined, in a manner as noted below. Thus, if a user is determined at baseline to have a particular ailment, a particular test may be administered to the user to define more precisely the user's disease state. Branching logic may define multiple sequential changes to the presented and collected data as disease or symptoms progress. By way of further example, if a user is determined to have a mental illness, such as negative symptoms schizophrenia based upon the baseline analysis, it may be determined to administer additional, more in depth instruments to the user in order to define more precisely the disease state, and progression of the disease, of the user. Once a predefined additional progression has been observed, further presentation of material may be provided that is determined to be better applicable to later stages of such a disease. Once implemented, processing passes to step 1790, also representative of step 1650 of FIG. 16, where baseline data is preferably updated in accordance with this updated data presentation and collection.

Information Capture System

Referring next to FIG. 1, a data capture and transfer system constructed according to the present disclosure is shown. In FIG. 1, a remote information capture apparatus 100 is first shown. Such information capture apparatus 100 is adapted to allow for the capture and processing of information in order to implement the system and method in accordance with the present disclosure, such as capturing one or more images of a patient administering medication, responding to presentation of one or more images or other stimuli to the patient, or conducting an adaptive, simulated interview with the patient. Such information capture apparatus 100 is preferably placed in communication with a remote data and computing location 300 via a communication system 200, preferably the Internet or other communication system. Via communication system 200, information captured by apparatus 100 may be transmitted to remote data and computing location 300, and analysis information or other instructions may be provided from remote data and computing location 300 to apparatus 100.

Remote data and computing location 300 may further process information received from information capture apparatus 100. Such processed information may preferably be provided to a remote information display device 400 via communication system 200. Remote information display device 400 is further adapted to receive input from one or more users to provide the received input back to remote data and computing location 300, via communication network 200, in order to direct the processing of received information by remote data and computing location 300. The processing by remote data and computing location 300 may further be conducted in accordance with information received from information capture apparatus 100, information pre-stored to remote data and computing location 300, and other information that may be provided via remote information and display device 400.

One or more patients of a plurality of patients may employ an individual information capture apparatus 100 in order to provide information specific to that patient to remote data and computing location 300. Therefore, in addition to capturing data related to the activities performed by the patient in response to one or more prompts provided to the user patient information capture apparatus 100, each corresponding information capture apparatus 100 may capture one or more passive activities performed by the patient while the patient engages the information capture apparatus, as will be described. Similarly, one or more remote information and display devices of a plurality of remote information and display devices 400 may be employed by a corresponding one or more users, each requesting different processing by remote data and computing location 300.

It is further contemplated that a plurality of such information capture apparatuses 100 may be coordinated to monitor a larger space than a space that can be covered by a single such apparatus. Thus, the apparatuses can be made aware of the presence of the other apparatuses, and may operate by transmitting all information to one of the apparatuses 100, or these apparatuses may each independently communicate with remote data and computing location, which is adapted to piece together the various information received from the plurality of devices 100, whether such information is prompted by information provided by information capture apparatus 100, or information is captured passively. These multiple apparatuses may be employed in a system allowing a user to log into any such system, or one in which tracking of a user through the fields of view of multiple devices may be desirable. Finally, it may be possible for data to be transmitted along devices (i.e. daisy chain) to allow for transmission of data from a device that does not have excellent communication system service to one that does. Information capture apparatus 100 may also perform local processing on collected information at information capture apparatus 100, and therefore forward pre-processed information to remote data and computing location 300. Remote data and computing location 300 may also comprise a data storage repository, or may be omitted, so that all processing is performed on information capture apparatus 100.

Figure 2:
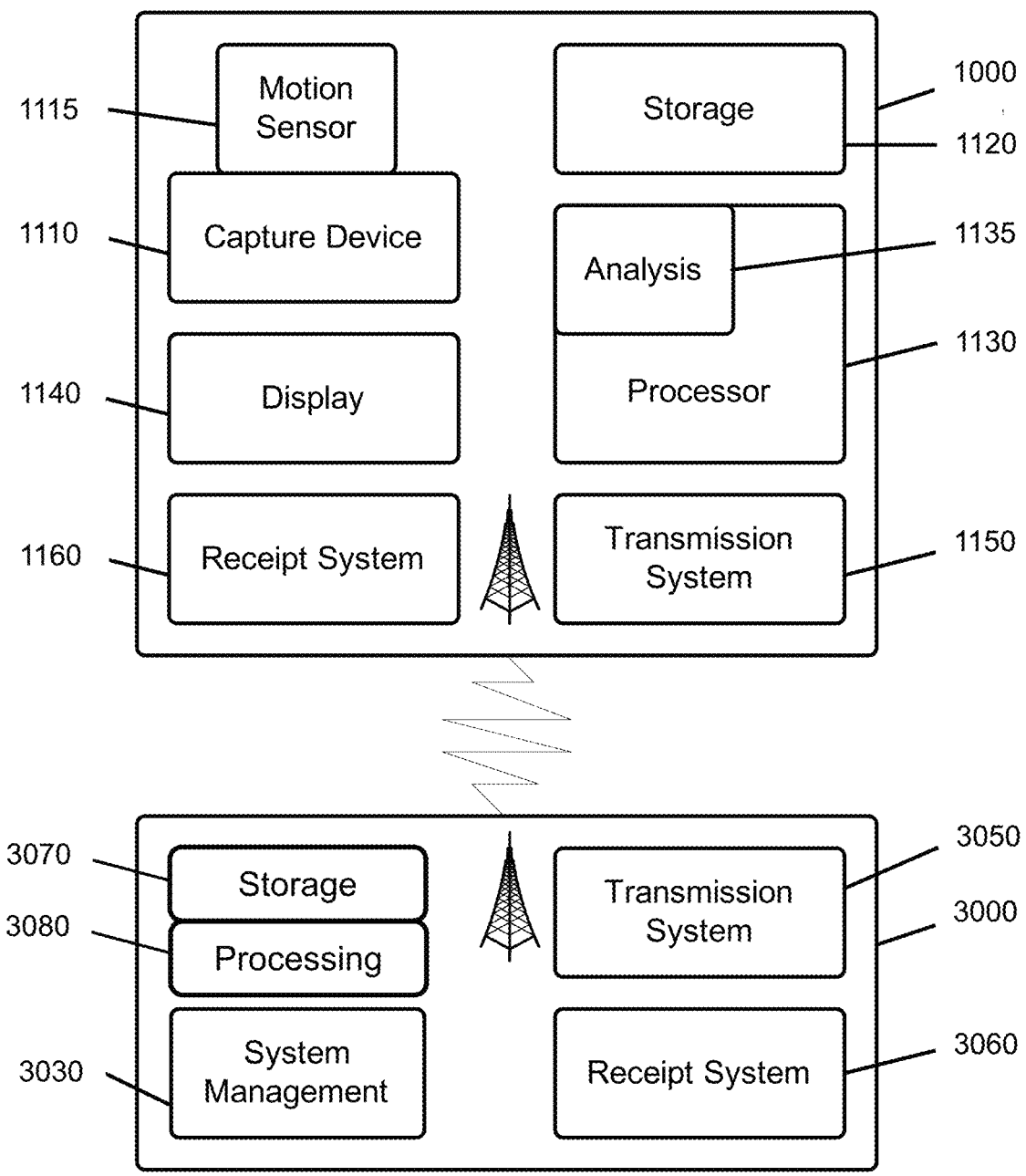
FIG. 2 depicts more detailed elements of the data capture and transfer system of FIG. 1.

Referring next to FIG. 2, a more detailed view of an exemplary embodiment of remote information capture apparatus 1000 (as an example of apparatus 100) and remote data and computing location 3000 (as an example of location 300) is shown. As is noted in FIG. 2, apparatus 1000 comprises an information capture device 1110 for capturing video and audio data as desired. A motion detector 1115 or other appropriate trigger device may be provided with capture device 1110 to allow for the initiation and completion of data capture. Information capture device 1110 may further comprise a visual or audio/visual data capture device, such as an audio/visual camera, or may be provided with an infrared, night vision, ultrasonic, laser, 2D, 3D, distance camera, radar or other appropriate information capture device. Motion sensor 1115 may also be used as an information sensor, the collected motion sensing information being provided with other collected information. Motion sensor may also be substituted with other sensors, including GPS sensors, accelerometers, rotational sensors, or other sensor related to the patient employing apparatus 1000. A storage location 1120 is further provided for storing captured information, and a processor 1130 is provided to control such capture and storage, process collected information, as well as other functions associated with the operation of remote information capture apparatus 1000. An analysis module 1135 is provided in accordance with processor 1130 to perform a portion of analysis of captured information at the remote information capture apparatus 1000. Apparatus 1000 is preferably further provided with a display 1140 for displaying information, and a data transmission and receipt system 1150 and 1160 for communicating with remote data and computing location 3000.

Remote data and computing location 3000 preferably comprises system management functions 3030, and a transmission and reception system 3050 and 3060 for communicating with apparatus 1000. Transmission and reception system 3050 and 3060 may further comprise various GPS modules so that a location (if provided as a mobile device) of the device can be determined at any time, and may further allow for a message to be sent to one or more individual apparatuses 1000, broadcast to all apparatuses in a particular situation, or being used for administration of a particular prescription regimen, of broadcast to all available apparatuses. Remote computing and data location 3000 may be further provided with data storage elements 3070 and processing elements 3080. Data storage elements 3070 preferably comprise one or more conventional storage units, and may be set up as a cloud computing system, or offline storage. Data storage elements 3070 are designed to receive the information collected above, and further to provide inputs of data into processing elements 3080. Such elements may comprise individual central processing units, graphical processing units, or other processing elements known to one of ordinary skill in the art. Remote computing and data location may further include at least a processor and analysis module, and a display, if appropriate. In accordance with an exemplary embodiment, apparatus 1000 is adapted to be part of a system that automatically monitors progression of symptoms of a patient in a number of ways, and may be employed during use of a medication adherence monitoring system relying on visual, audio, and other real time or recorded data. The system may similarly be employed to collect information from a user separate from use during medication administration. Users of apparatus 1000 (patients) in accordance with the disclosure are monitored in accordance with their interaction with the system, and in particular during medication administration or performance of some other common, consistent activity, in response to presentation of visual material to the patient, or during the conduct of an adaptive, automated interview with the patient in a manner as described above with respect to FIGS. 16 and 17. Apparatus 1000 is adapted to receive instructions for patients from remote data and computing location 3000 and provide these instructions to patients. Such instructions may comprise written, video or audio instructions for guiding a patient to perform one or more activities, such as determining whether a patient is adhering to a prescribed medication protocol by presenting a correct medication to the system, instructions and visual images to be provided to the patient so that a response may be measured, or instructions that are adaptive in order to allow for the conduct of an adaptive, automated interview with the patient.

Remote Information and Capture Apparatus

Figure 3:
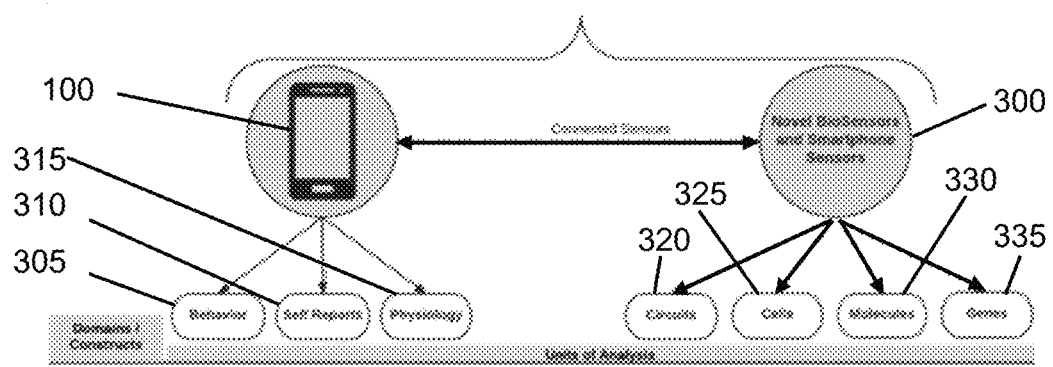
FIG. 3 depicts a hierarchy depicting availability of commoditized sensor data.

The described system therefore includes three main components, data collection, data storage and analysis, and a mechanism for receiving user input to pose a query, and to provide responses to the posed query after performing an appropriate data analysis. Referring next to FIG. 3, the data collection component will first be described. FIG. 3 depicts a relationship between an information hierarchy of information that is available from conventional sensor data associated with a standard remote information capture apparatus 100, including one or more sensors for the collection of conventional sensor data, and a hierarchy of information that is available from advanced sensor data associated with an advanced remote information capture apparatus 100, including one or more further advanced sensors for the collection of advanced sensor data, such as data that may be collected by remote information capture apparatus 100, is shown. FIG. 3 depicts sensors and data they capture, including sensors that capture behavioral data 305, self-reported data 310, and physiological data 315, and additional advanced novel biosensors and smartphone sensors that may monitor circuits or other electrical inputs 320, cells 325, molecules 330 or genes 335 and how this collected sensor data may be integrated via connected sensors, on order to fine one or more correlations between these sensors. By way of example, behavioral sensors that collect behavioral data 305 can be GPS sensors, accelerometers, or other sensors included within apparatus 100, Bluetooth connectivity and call logs, for example. Self-reported information may be collected via real time surveys presented to a patient. A final conventional group of sensors for collecting physiological data may include a heat rate monitor, a skin conductance meter, a respiratory rate measurement device, or a mechanism for confirming a startle reflex, by way of example. Additional novel bio and smartphone sensors may use, e.g., real time EEG sensors (sensors 320), one or more mechanisms for performing direct testing on the cells 325 of a patient, one or more molecular sensors (330), or one or more gene chips or other gene sensing technology 335.

The depicted information relationship shows the sharing of information and analysis in accordance with the data collected from standard sensor sources, such as GPS data, accelerometer data, self-reports and the like and the more advanced sensors. While these big, commoditized and accessible data sets are prevalent in use, they do not allow for in depth analysis that would support medical-grade solutions, such as the ability to accurately monitor changes in symptoms of disease and to diagnose the existence and progression of disease. With the systems and techniques disclosed herein, various symptoms, which are potentially indicative of a disease state, may be monitored, through the processing of known data sets. As shown, each potential symptom is tied to a particular measurement. While these measurements may give some insight, there is no mechanism for combining these measurements, or for making more measurements based upon inventive tests, such as those proposed in accordance with the present disclosure.

Therefore, in accordance with the various embodiments of the present disclosure, the systems and methods disclosed herein may provide for novel testing and collection of advanced visual and other sensor data, and also for advanced analysis of the collected unique data. As will be described below, collection of such data may be performed in both active and passive modes, and may also allow unique, automated interaction with a user so that the data may be extracted in a most efficient manner, while tailoring the data collection process based upon the results of earlier data captured during the process.

Once collected, data across multiple patients or users may be compiled to allow for further analysis. The collected information may be analyzed along a plurality of dimensions so that expected changes along each of those dimensions may be determined. One or more patients may be characterized as reacting to changes along one or more of these dimensions. Other aspects of the demographic information for each of the patients may provide the ability to recognize characteristic changes along each of those dimensions categorized by the demographic of the patient. Thus, by collecting information (e.g., patient symptom information) across all patients, categorizing the data by demographic, and analyzing the categorized data, predictions of future expected responses across these same dimensions can be determined.

In a still further aspect of the present disclosure, potential future expectations of medication responsiveness may be determined based on patient demographics by categorizing patient responses to the administration of medication along the different demographic group dimensions and by determining aspects of medication responsible for changes to the characteristics along these same dimensions. The systems and techniques disclosed herein can be used as a medication identification tool by searching a desired combination of patient results to provide a guide for medications to be used to combat certain of the symptoms matching the dimensions.

In accordance with one or more embodiments, data is collected and may be correlated to disease progression and allow for an in-depth analysis of disease as it progresses through to all stages and exhibits all symptoms of those stages. If such data is collected via an automated active process, where one or more questions or other stimuli, are presented to a patient, a data sensitive process is employed where branching logic may dictate not only a next question to be asked of a patient after a response to a prior question, but also may dictate the actual visual and other sensor data to be collected based upon a response to a prior question, data received from a sensor, or near real time, or asynchronous analysis of previously collected visual and other sensor data. In such a manner, in accordance with an exemplary embodiment, if a patient is monitored in an automated fashion to determine a response to a particular stimulus, such as being shown a particular image to elicit a response, the system may output to a display and based upon a response to the first image, a second image, in which the particular second image chosen to be displayed depends on the specific response of the patient to the first image. Alternatively or in addition, if a user ingesting a medication pill is being monitored, and the system determines that the user is having trouble swallowing the medication pill (e.g., where the system makes such a determination in an automated fashion in accordance with artificial intelligence and computer vision analysis of data collected by one or more data collection devices as described above), the system may focus the collection of high resolution video data onto an area of the throat of the user in order to analyze micro-movements of the throat of the user to confirm actual ingestion.

In accordance with one or more exemplary embodiments, analysis and care pathways may be defined, and implemented in near-real time, while the system is automatically interacting with a patient during a single session (i.e. while the user is still interacting with the system, such as in near real time, as opposed to a system that collects data during a session, analyzes the data offline, and then provides a response at a later time), for example, in order to efficiently guide the patient to perform a desired sequence of steps, and to focus data collection and the steps to be performed to allow collection of data that may be most relevant to supporting analysis of a particular symptom or component of disease. For instance, a patient with Parkinson's disease, may warrant analysis of changes in consistency of a hand tremor, for example, as identified in an automated process in accordance with one or more embodiments. Upon indication of a desire to monitor such a disease by a provider of the monitoring system, which may include doctors, other healthcare providers, clinical trial sponsors, contract research organizations, and the like, data collection may be focused by the system on those aspects that are related to such hand tremor, in that it has been predetermined that tremor is a correlated indicator to progression of Parkinson's disease. In addition, for example, upon automated identification of changes in or an absolute level of such hand tremor based upon data collected by the system, different analysis pathways may be initiated so that slight tremors or slight changes in tremors, the system may output requests for the patient to perform certain sequences of actions, while testing of more intense tremors may involve the system outputting requests for the patient to perform different sequences of actions to allow for different testing. Additional details of particular data to be collected will be described below.

Aspects of the disclosure therefore allow for movement from a system where known measurements are used to provide known insight to one in which novel measurements may be collected from a user, and novel, insight be gleaned from those novel measurements. The system described in accordance with this disclosure devises a novel measurement, and based upon this novel measurement, provides a novel insight. Thus, at least the combination of novel measurements and insights differentiates the subject matter of the present disclosure from alternative systems for analyzing patient states. The systems and techniques disclosed herein may rely on both active and passive data collection via apparatus 1000, for example, as will be further described below. Active data collection may comprise, e.g., an automated interview (e.g., where questions are presented to a user and answers to the questions are recorded), an interactive test, a self-assessment, or other interaction where material, stimulus, or prompt is actively pushed to the user to elicit a response to the material, stimulus or prompt. Passive data collection comprises, e.g., automated video analysis while a user is performing some other action, such as dosing, or administering their medication while engaging with a medication monitoring system (such as a visually based medication adherence monitoring system, such as that provided by AiCure®), using one or more sensors to collect data, or collecting visual or other data at any time while the user is performing some action not elicited solely for the purposes of collecting the test response data.

In addition to using the collected test response data as noted herein, the collected data may also be used to aid in confirmation of medication administration. Patient response to medication administration in accordance with any of the measured parameters noted above may be predicted, and then explored for new patients. Combining expected responses of any number of symptoms may be employed in order to provide multiple redundant layers of medication administration confirmation. In accordance with an exemplary embodiment of the present disclosure, sensors such as those used in a mobile phone or other device, including two dimensional and three dimensional cameras (e.g., for time of flight calculations) may be employed. Any of the following signals may be monitored to confirm one or more elements indicative of proper medication administration: hand gestures, head tilt, Gulp (swallowing), movement of jaw, grip of pills, timing of performance of one or more if these actions, movement of shoulders, strain of the patient's neck, changes in breathing, pupil control, changes in blinking speed and consistency, fluttering of eyes, any other indication of physical strain, and the like. Further in accordance with active analysis as noted above, it may be further possible to monitor the following: 1) expressivity (including the level or amount of animation when smiling, frowning, etc.), 2) movement (tremors and motor control), 3) concentration (including gaze), 4) facial control (including eye movement and blinks/twitches/paralysis), 5) cognition tasks (ability to read a paragraph), 6) visual breathing rates, 7) body mass changes, 8) facial wasting, and the like. These and other physiological changes may also be evaluated based on, for example, triangulation of skin using a depth sensor (a time of flight camera) to see flow of blood to measure clots or even heart rate. Blood pressure may be measured by scanning how the face of the patient has changed, or by looking beneath the skin to monitor capillary flow or blockage. Changes in such abilities may be therefore be indicative or progression of disease, and effectiveness of medication administration.

Additionally, in accordance with the second aspect of the invention, as will be described below, the collected data from any of these sources may be captured for more advanced analysis, including analysis based upon predetermined requests for information included in remote data and computing location 3000, or in response to near-real time requests from a user via remote information and display device 400.

Figure 4:
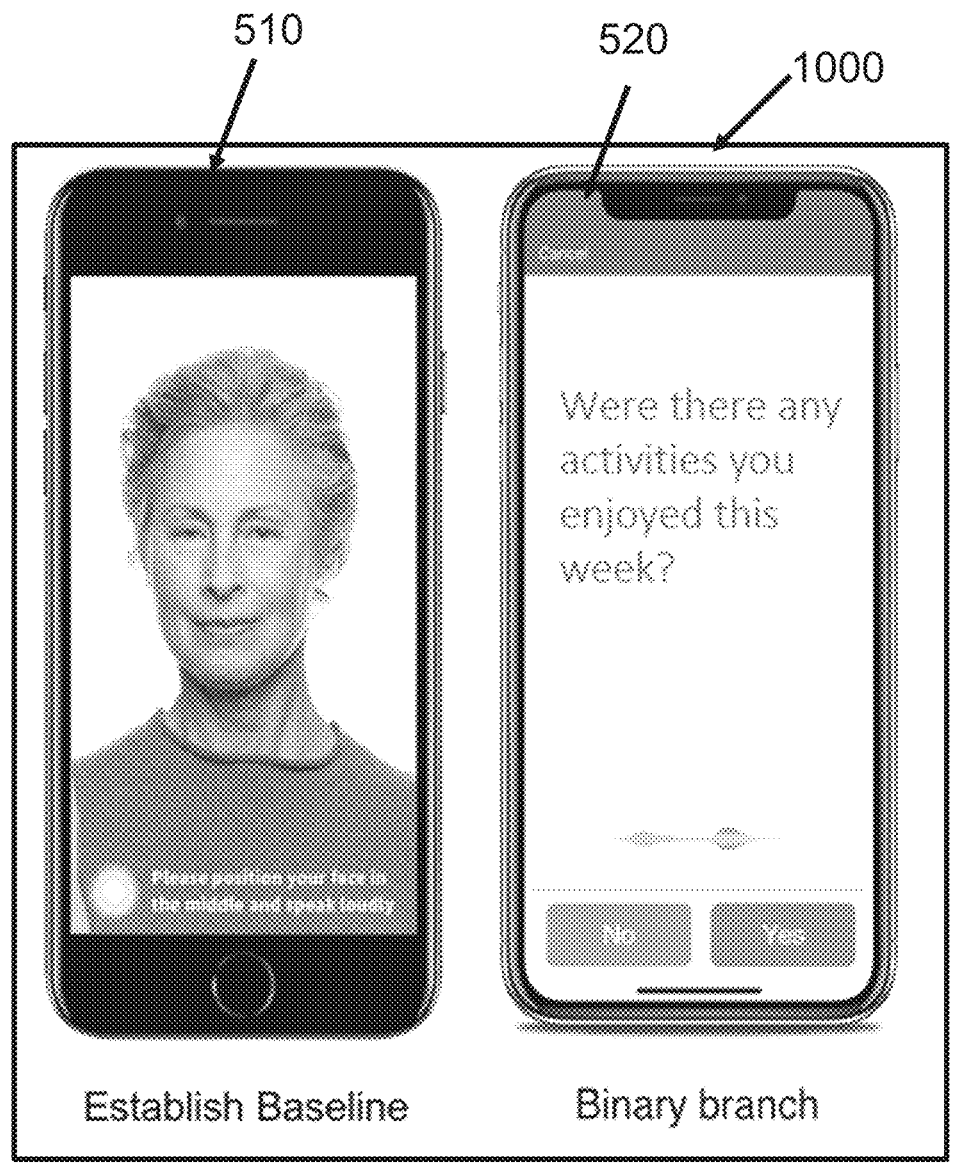
FIG. 4 depicts a first portion of a sample interview.
Figure 5:
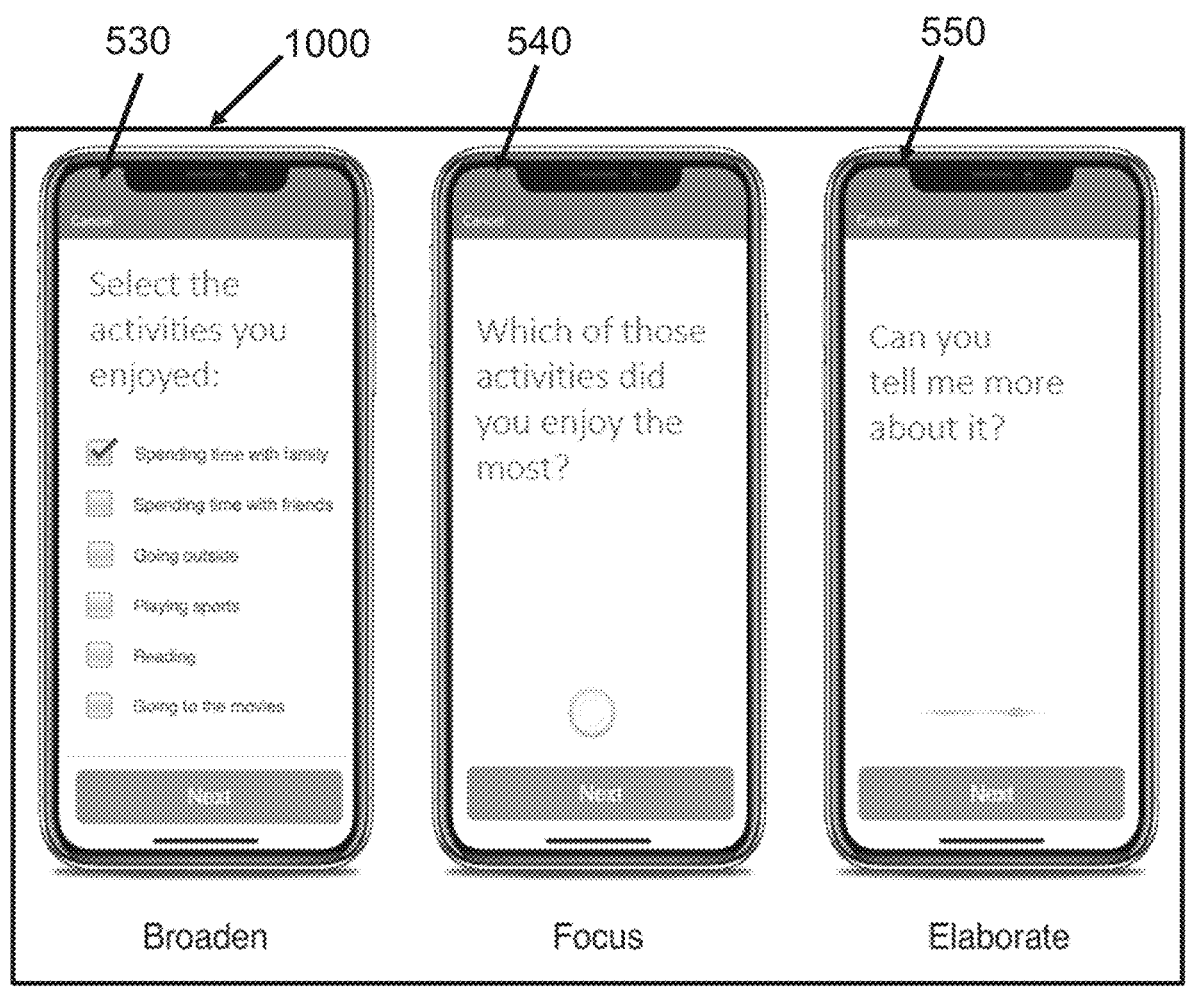
FIG. 5 depicts a second portion of a sample automated interview.

Referring next to FIGS. 4 and 5, details of active mechanisms for collecting data from a patient will be described. These mechanisms should be considered examples, noting that any reference to numbers of presentations, or any particular language employed is exemplary only, and that other questions, images or the like may be employed. As is shown in FIGS. 4 and 5, at step 510, a user is first preferably requested to position their face in the middle of a field of view of an image captured by a camera and as displayed on a display of a device, such as device 1000 (see FIG. 1). The purpose for such placement in accordance with an embodiment of the invention may be to determine a baseline visual view of the face of the user. As will be described below in greater detail, this baseline may be determined from a single image/video collection or may preferably be determined in accordance with a plurality of image/video baseline collections, and in a manner as described herein. If determined in accordance with such a plurality of image/video baseline collections, if is also therefore possible to determine whether the current baseline is in line with the other collected baselines, or whether the user is already showing differences from their average baseline, and a transformation or adjustment should be made.

Once the baseline has been collected, as shown in FIGS. 4 and 5, a first question from a binary branch of questioning logic is asked at 520. A sequence of predetermined questions or a branching logic associated with the baseline questions may be presented as an instrument designed to diagnose a particular disease or determine progression of disease or one or more symptoms associated therewith. The sequence of questions is important, as determined by the inventors of the present invention, in order to provide a more natural interview process to the user. Thus, in some implementations, a relatively broad question is asked first. The user is then asked to answer the question using the touch screen buttons, and verbally. In an exemplary embodiment, video may also be recorded of the user to allow for subsequent analysis of that video to assist in determination of progression of symptoms, or diagnosis of disease.

At step 530, based upon the response provided at step 520, an additional question may be asked in an automated fashion, requesting additional information in response to the prior question. In the example shown in FIGS. 4 and 5, if the user answers yes to whether there were any activities that the user enjoyed over the weekend, the user may then be asked to respond, using the touch screen of device 510, a question designed to broaden the ideas that they are thinking about and may also be prompted to provide a verbal or visual response. For example, the user may be asked to select, from a list of activities, an activity that the user enjoyed. This question allows for active monitoring of other actions or characteristics of the user after branching logic is applied. After completion of the broadening question, a more focused question is noted at step 540 in order to draw the user further into the conversation. The response at this point is preferably verbal and visual. Finally, after providing the focused response, the user may be asked to elaborate in order to further draw the user into a conversation and avoid the impression of a system that is simply recording.

The sequence of questions may be based upon any prior questions and may also be based upon analysis of the audio and video responses received from the current patient using the system. While the answers to the questions may provide some information about the user, in accordance with an exemplary embodiment of the present disclosure, it is the analysis of the audio and video responses that is most important. Indeed, the actual wording provided by the user may be unimportant. Rather, by drawing the user in to a conversation in an automated fashion, the system is able to further analyze the received audio and video sequences in order to determine mood, feelings, progression of symptoms of any sort, or development of disease based upon these symptoms. How the user performed any set of tasks such as interacting with the touch screen or other requested tasks is as important as the types of answers provided. Additionally, the method in which the responses were described can provide significant insight into the current mood of the subject.

The systems in accordance with an embodiment of the present disclosure are therefore enabled to conduct automated, intelligent interviews, and to also extract and analyze visual, temporal, gestural, prosodic & natural language data, as will be described below. As also noted above, intelligent interviews may be performed by asking questions of the user, evaluating responses, and branching logic based upon the responses. In such a manner, a realistic interview is provided in which the user is encouraged to engage most completely with the inventive system to allow for the greatest amount of analyzable data to be collected.

In accordance with an alternative embodiment, rather than having the user interact directly with the device 1000, an interviewer may rely upon device 1000 to present to the interviewer the questions to be asked of the user. The responses to these questions may be provided verbally, or also including video capture. Thus, after the interviewer asks a question, the audio and/or video responses may be collected and analyzed in near-real time, thus allowing for a next question to be presented to the interviewer to ask the user. The analysis of the audio and video may similarly be performed at a remote location (3000), thus allowing for a second, more in-depth analysis, or may be provided in real time if connectivity is good, and the local device with which the interviewer/user is interacting is unable to properly process the information.

Remote Data and Computing Location

The data noted above and as further described below is preferably collected to create a database that may be indexed by any number of dimensions, but preferably and initially by disease indication. While it is possible that all processing may take place at a local device of the user, or alternatively all processing may take place at a remote location with the mobile or other local device only acting as a data capture device, interaction with a local device of the user allows for near-real time interaction with the user, even if there is no communication network connection, and further in depth analysis at a later time in an asynchronous manner. Subsequent indexing may be performed by patient demographics and patient response to medication administration. When a new patient is introduced to the platform to be monitored taking their medication, the system can first be employed to identify any particular risk that the patient may encounter, based upon any indexed dimension of the patient. The system therefore provides an early warning system related to potential patient response to a particular medication. Therefore, not only can the system be used to monitor an upcoming patient into the system taking particular medication, but also can be used to determine a potential response of a theoretical patient to a particular medication to be administered. In this manner, quality of response (whether positive, indicative of efficacy of a medication, or negative including the likelihood of an adverse reaction) to a particular medication may be determined.

Other aspects of the patient response to the medication may also be predicted based upon the patient demographics and the database of prior patients' responses, and the prior response of the particular next patient, if that patient is already in the database. Thus, disease symptom progression may be predicted, and may be adjusted based upon expected medication response. Deviation from the expected symptom progression as determined in an automated fashion by the present systems may indicate a parallel deviation from the required medication administration protocol, or an atypical response of the patient to the medication. Further, a predicted impact (i.e. comparing a measured value or values to an expected value or values as determined from prior data captures) on the computational diagnostic measures described above, whether collected actively or passively, may be provided. The results of such an analysis may be converted to an efficacy score, indicative of the effectiveness of the medication based upon the various dimensions of the patient. Values may be combined across measurements into a single score indicative of effectiveness of the medication. Two drugs, one that greatly improves tremor, but does poorly with fine motor control, and another that is the opposite may have similar efficacy scores, because they both improve conditions. The true benefit of the system is to try to recognize the features of the first drug that improve tremor and the features of the second drug that improve fine motor control, and search for a new drug having these two features so that a better drug with higher efficacy score overall can be discovered. Thus, for future patients, measurement of a number of parameters may allow for the prediction of how effective a medication may be for a particular patient, and ultimately may allow for the selection of one medication over another based upon the demographics or other measurements of the subject, and similarly may be able to predict the response of the patient to the measurements noted above. Such comparisons may be performed during the entire term of medication administration, and may allow for monitoring of disease progression, and perhaps suggest when changes in medication protocol may be justified. Once accumulated, such a database may be available for use in order to aid in predicting patient response to other medications that may be under development. For example, a scoring system may be created to show effectiveness and safety of a particular medication in comparison to predecessor drugs or other treatment options that have gone through the system when presented with a particular disease or therapeutic area. Additionally, a measured response of patients to a particular drug may allow for prediction as to how similarly-situated patients may respond to another drug, or alternatively, how other patients may respond to the same drug. Through analysis, other patients having similar responses on one or more particular dimensions may allow for prediction of successful response to the drug, for example. In this manner, predictability of response to a drug may be available based upon similarity of patients on the most critical dimensions.

In accordance with alternative embodiments, rather than simply determining one or more correlations between patient demographics and expected responses to the one or more testing scenarios noted above, similar correlations may be determined to one or more gene expression profiles. Gene expression profiling is a high throughput approach to analyze the expression of tens of thousands of genes simultaneously. Expression of specific groups of genes, or gene expression profiles, can then be correlated to pathologic diagnosis, clinical outcomes, or therapeutic response. Transcriptional profiling experiments can be used to generate compendia of gene expression data across different cell types, development times, and in response to distinct stimuli. A similar application of this determined gene expression and gene transcriptional profile in accordance with one or more embodiment of the present disclosure correlates to movement signatures, symptom progression, or other expected or observed responses in accordance with the active or passive measurements noted above, based upon one or more individual or sequentially-applied measurements.

In accordance with another aspect, through the use of remote information and display device 400, not only can collected data be pre-processed to provide one or more predetermined analysis results, the system may preferably be adapted to receive user input data from an external user directing one or more queries related to the collected data. Thus, in accordance with one or more embodiments, a user may present a patient profile to the system via a remote information and display device 400 and evaluate how the patient may respond to a plurality of medications. As noted above, a plurality of medications and the response of a plurality of patients may have been previously captured. The profile of each patient may be dissected into a plurality of components related to their improvement over a plurality of different dimensions, and also based upon simpler demographics, or more complex disease state or characteristics, and each of these components catalogued. Thus, when a user queries the system, it is possible to provide a demographic profile of a potential user and determine how that user might react or respond to any number of these stored medications.

Furthermore, in addition to dissecting the profile of each patient, the profile of each medication may similarly be dissected. Thus, each medication may be measured along a plurality of dimensions in order to determine characteristic of that medication. These measured characteristics may then be used to predict which medications may be applicable to particular disease or patient populations. Thus, by way of example, measured medication characteristics may include 1) their sedative effect, 2) the ability to reduce paranoia, and/or 3) ease of application, among others. If one is then looking to find a medication for use in a particular population, medications that have a low sedative effect while reducing paranoia, and that are easy to administer, may prove to be a winning combination. Drugs having these characteristics can then be investigated as potentially effective in this population.

In this manner, users may be given access to remote information and display device 400 as an analysis tool that interacts with and performs requested analysis on the data stored in remote data and computing location 300 after collection by remote information and capture device 100. This interface into the complex system preferably provides a simple yet robust system to determining potential patient response, and for drug discovery, without the need for the user to collect, understand, or independently analyze the collected data. Rather, a simple interface allows these users to easily pose complex queries to the data and be presented with results determined through the user of a complex artificial intelligence-based system.

The following description of analysis of users may be performed in accordance with the active presentation of information (as described) but may also be utilized in accordance with a passive data collection. In such a passive environment, identification of the timing of triggers is more important, as they are not predetermined. The described collection of data is an example of collection of data to be provided to remote data and computing location 300.

Data Collection System Example

Figure 6:
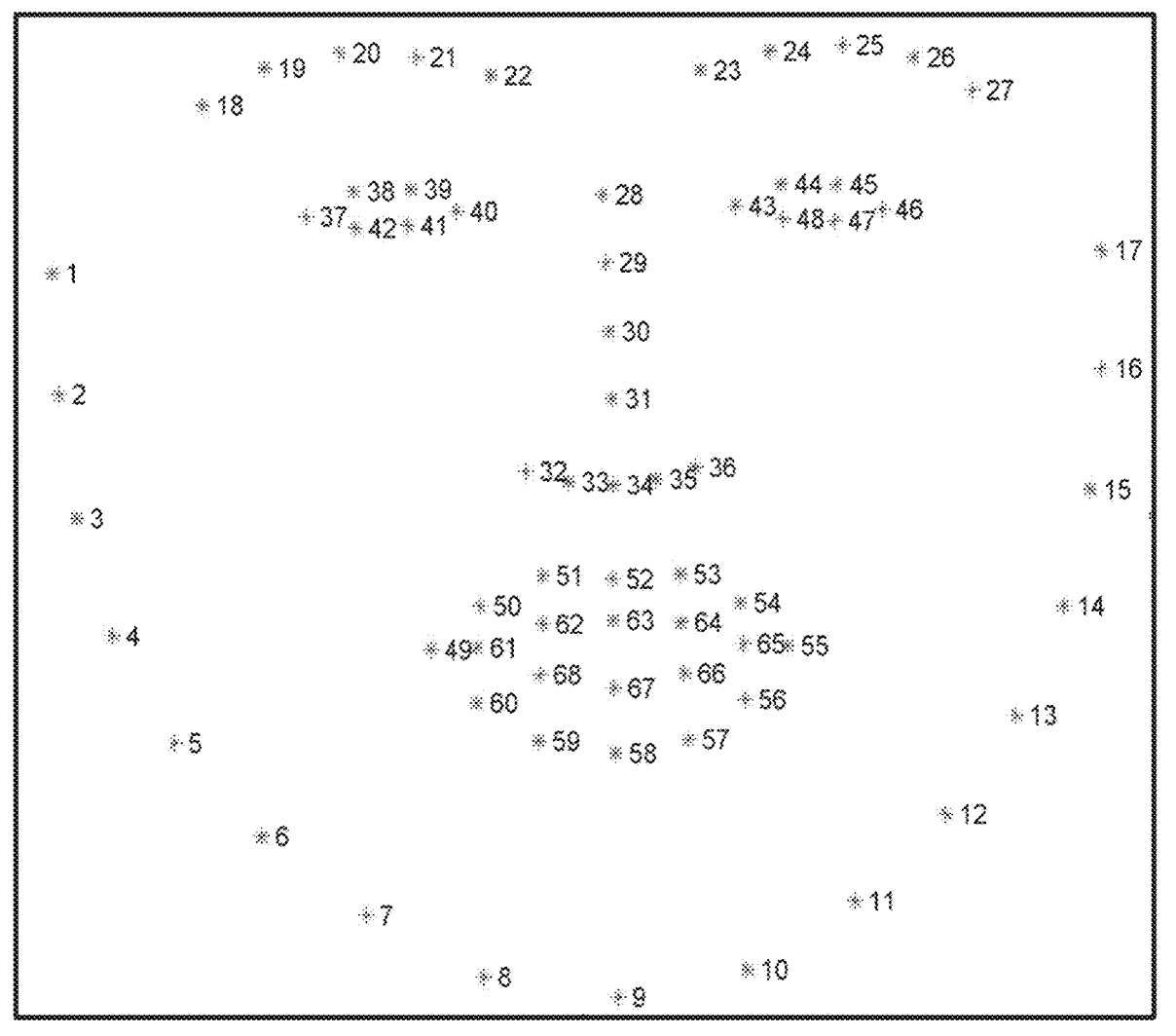

Referring next to FIG. 6, a system for designating action units on the face of a user is shown. In FIG. 6, multiple different points (e.g., 68 different points) on the face of a user are defined. While any particular points may be defined, the number and location of the points may be selected based on the desired attributes of the user to analyze. For instance, the 68 points shown in FIG. 6 (also known as keypoints or landmarks) allow for robust tracking of action units of the face, and thus providing the ability to analyze facial expression without overwhelming the system. Each of these points may be measured to determine its movement during performance of one or more activities, such as in response to the presentation of one or more stimuli to the user. As is known in the art, when a particular action unit moves (action units may comprise a single or multiple points, keypoints or landmarks), it is possible to measure this movement. However, if the action unit moves too far from an expected "neutral" location, the system breaks down and the action unit cannot be recognized. However, rather than using as a "neutral" location system an average mask across all users, the system of the present disclosure relies on a more customized mask for the individual user. Thus, by setting a baseline positioning of the action units of a particular user, it is possible to better account for differences between the face of a particular individual. Such a baseline position may be defined by providing a basic set of images or other material to a user and measuring the response of the predefined action units. By presenting this consistent "calibration" set of images or other stimuli it is possible to then determine an expected movement of the action units, and then determine a relative movement when further unique or different images or stimuli are provided. This allows for a user with relatively low action unit movement to be judged against this expectation, while an animated person will be judged against this more animated expectation. Thus, the expected movements may also be tied to a particular individual, thus allowing for more flexibility in tracking the action units as the subject is provided with one or more stimuli.

Also, it has been discovered that it is possible to identify which of the presented action units (or other appropriate measurement points or values, including but not limited to keypoints, landmarks (as represented by the points in FIG. 6, and preferably comprising one or more points on the face of a user that may be indicative of movement of the face that may be of interest to a reviewer, typically indicative of changes in facial expression), shapes, textures, poses, features from both 2D and 3D sensors) are most likely to be important when reviewing progressions for a particular disease or symptom, for example. Based upon the desired action units, it is therefore to focus on only these action units, and not measure the others. Thus, a context-sensitive system may be provided in which a priori knowledge about a particular therapeutic area or disease state may allow for the focusing of the system on the action units most likely to give valuable information. Additionally, it is also possible, in accordance some embodiments, to vary the stimuli presented to the user in accordance with the desired information to be extracted, and also based upon therapeutic area, disease state, symptom progression, or the like. By way of example, it is possible to present images to individuals suffering from schizophrenia who typically present what is referred to as negative symptoms. They exhibit very low levels of action unit movement, and generally not an overly animated response. Because generating a response is the goal, extremely happy or disturbing images may be shown to a patient. For others with more standard response expectations, more mainstream images may be more appropriate. This feature selection step can be achieved through a combination of expert identifications and machine learning based approaches to derive more effective but non-intuitive features. This process may also be applied to other measurable quantities, such as level of tremor, voice inflection, volume, etc.

In accordance with some embodiments, daily or more frequent images of a user responding to baseline images may be taken for a baseline determination (step 510 above) in order to evolve the current baseline for a particular individual. The response of the patient to these baseline images may be averaged to obtain a customized baseline against which other collected patient responses to the presentation of future (e.g., the same images as the baseline images or different images from the baseline) images and action unit movement can be compared to measure changes in such movements. Furthermore, in addition to providing a custom baseline for each individual user, it is also possible to compare this customized baseline to an average baseline across all subjects in order to discern absolute information about the current status of the user relative to others in the same therapeutic area, or suffering for the same disease, by way of example. Therefore, daily monitoring of the user performing a repetitive task, such as administering a medication pill (for example) provides a visual baseline. Through observation of a user over time performing such a standard repetitive task, a baseline may be provided against which future data collection can be compared. Repetitive tasks also help identify the core symptom-related features and remove noise and variations in natural behaviors. The baseline may therefore not be based on just one measured instance, but may instead comprise a model learned from multiple instances of measurement. In this manner, deltas from an individualized baseline, rather than an average baseline can be determined.

Figure 7:
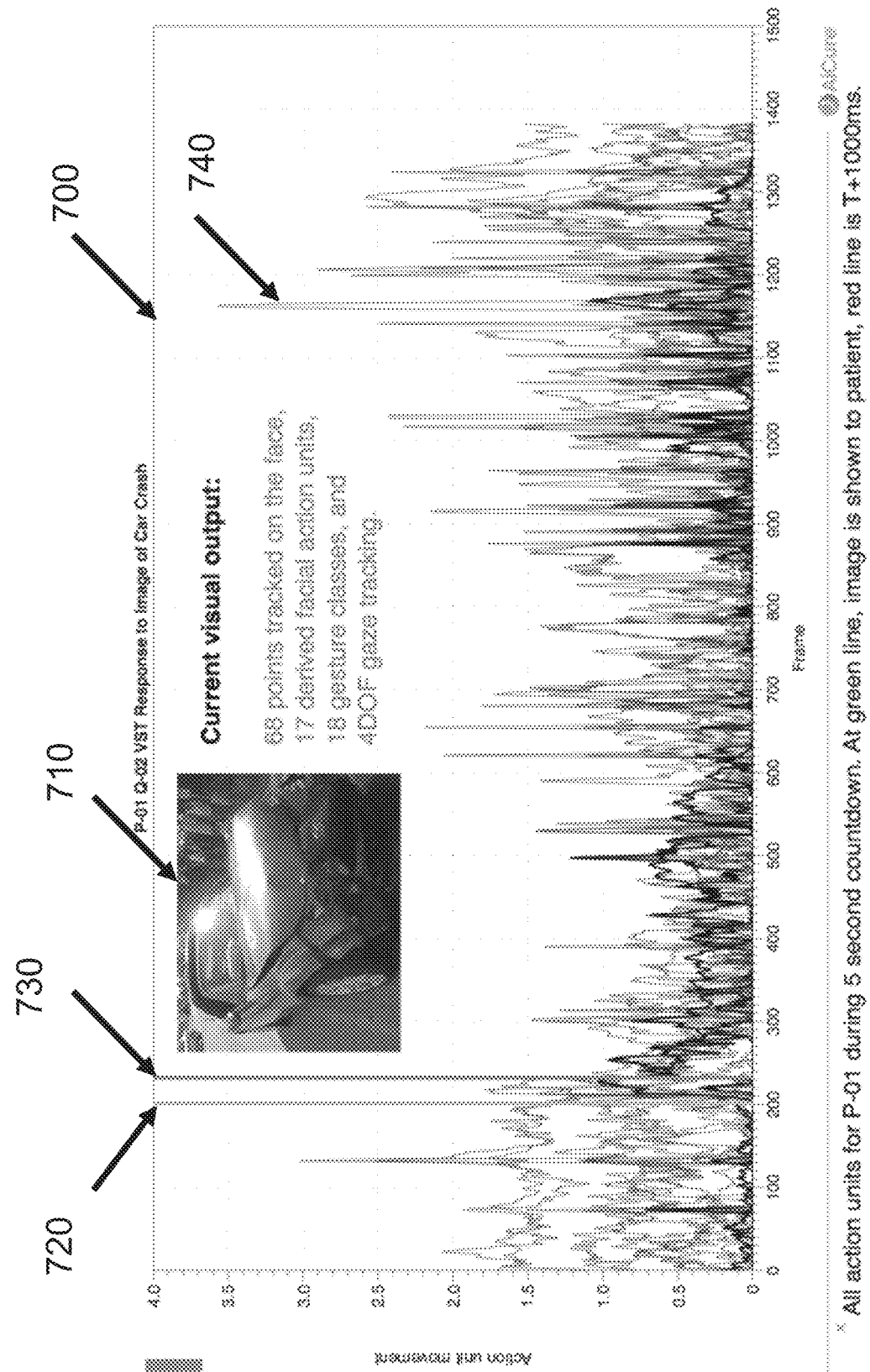
FIG. 7 is a graph representing the output employing the facial action coding system of FIG. 6, while a data subject is viewing an image of a car crash.

When a user interacts with the system of the present disclosure, the system may present the user with one or more types of stimuli (e.g., audio stimuli and/or visual stimuli). Such stimuli may comprise, e.g., a question or other prompt, as noted above, or may comprise the presentation of some visual or audio material that elicits a response from the user. Referring next to FIG. 7, a graph 700 representative of a response of a user to the presentation of just such a stimulus is shown. In the sequence of events leading up to graph 700 of FIG. 7, the system outputs to a display an image 710 for viewing by the user, in this case an image of a car crash. Traces 740 depict an amount of movement of one or more of the action units (1-68) shown in FIG. 6 from a baseline position. Thus, for approximately 1400 frames of video (x-axis) the movement of these action units is traced along the y-axis in the present example. A number of the 1400 frames are recorded prior to the presentation of image 710, which takes place at line 720. As is shown in FIG. 7, sometime after the presentation of the image 710 at line 720, the movement of the action units of the user are reduced, on average, as compared with the time prior to line 720. The system is therefore able to track all 68 points (or keypoints or landmarks) on the face of the user, deriving 17 facial action units (points that work together and are indicative of movement of a muscle structure of the face, such as when particular action units are engaged when a subject smiles, frowns, cries, etc.), determining 18 gesture classes (gestures that can be confirmed based upon actuation of one or more particular action units), and also employing gaze tracking to trace the direction of gaze of the user. By grouping the collected data on the movement of the data points, the action units can be determined. Movements of the action units can be analyzed to determine which are associated with the performance of one or more gestures, and those gestures can then be determined based upon monitoring movement of the points on the face of the user.

Moreover, it has been determined by the inventors of the present invention that the time between line 720 and a next line 730 (approximately 1000 milliseconds) is a portion of the timeline where the user's mind and body may present a response to the stimulus, but where the user has not yet consciously recognized the stimulus, or the user's response to this stimulus. Beyond this time, and thoughtful action takes over and guides the response of the user. It is this portion of the timeline (and more precisely, the first 250 milliseconds after presentation of the stimulus) that may provide the greatest insight into user response. This unique measurement is not able to be performed manually, as the human vision system is not able to see, recognize and remember facial movements over such a short timeline. Therefore, in some implementations, it may be advantageous to view the facial movements of the user using high speed photography at a frame rate more than double the common 24 fps frame rate, and preferably higher to allow for the collection of extremely short movements or gestures. Such a camera may be employed as part of a typical mobile device, or may be included as an add on, via USB or other common connector to the mobile device. The system may further be provided as a standalone system that includes a single purpose high speed camera, connected to a computer capture device in a traditional manner. in accordance with the embodiments of the present disclosure so that these small timeframes may be analyzed. These movements of the face in this minimal time frame are referred to as "microexpressions." Essentially, these microexpressions are presented by the face of the user before the user is fully cognitive of and able to process the received stimulus. By varying the window over which one looks at these microexpressions, the system can filter for different responses.

Figure 8A:
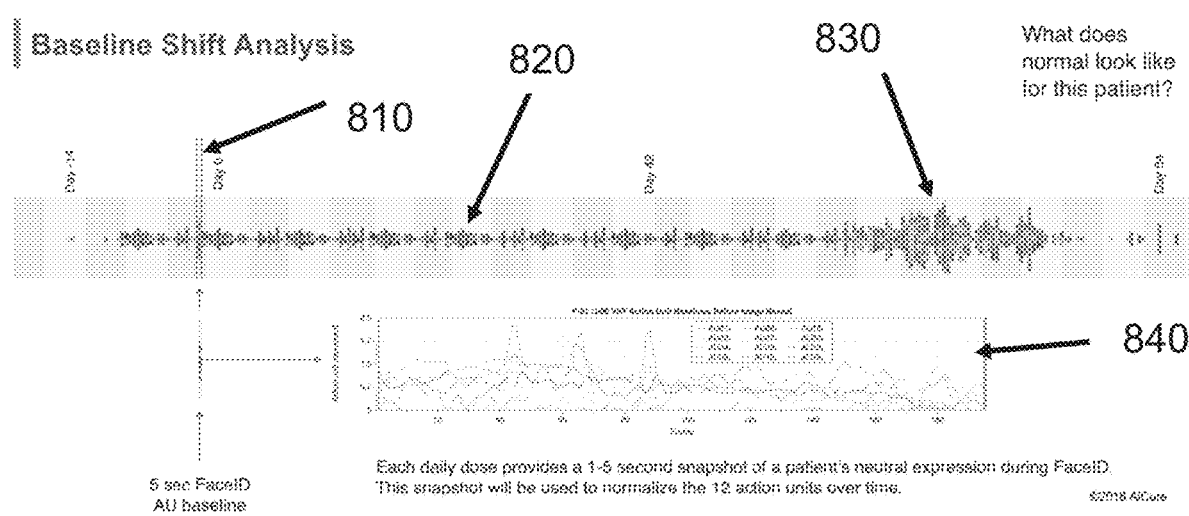
FIGS. 8A and 8B are graphs depicting an exemplary baseline shift analysis.
Figure 8B:
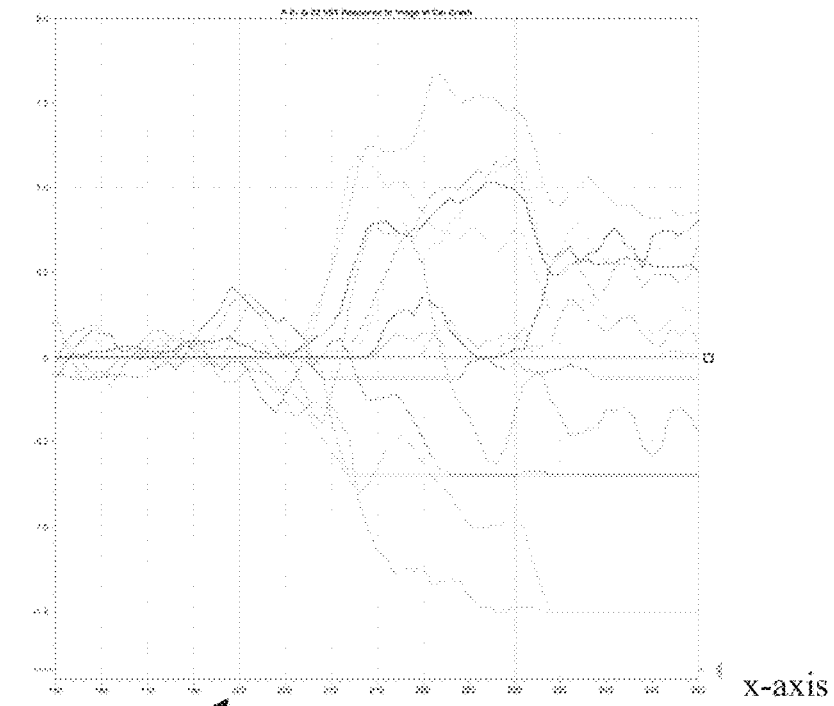

By accumulating multiple responses of a user to multiple stimuli, it is possible to build a profile of the user that allows for more complete understanding of the user's status related to symptoms and disease. It is important, as noted above, and as is further shown in FIG. 8A, determining a proper baseline for each user of the system allows for more customized review of future actions by that user. As is shown in FIG. 8A, a first baseline reading during a face identification may be performed at 810, generating a baseline analysis time sequence 820 across a timeline of any number of days, or other time measurement. This baseline analysis may also be performed while the user is speaking or performing an action, such as any action that may be considered a "background" action or situation (i.e. portions of the image that are not determined to be part of the user action being recorded, such as the wall, moving cars, etc. Thus, to remove the effects on measurements from simple talking, the user can be asked to perform a standard action for a baseline while talking. To remove the effects of walking, the user can be asked to set a baseline while walking, etc. As is shown in time sequence 820, initial baseline is consistent over much of the graph, but changes at point 830, indicating a systematic change for this particular user. Thus, a change in baseline of the user is quite evident, and may be investigated. Graph 840 depicts the material presented for each time period in the graph 820, and includes readings for a number of action units being measured. FIG. 8B depicts a resulting image after normalizing the baselines for all of the action units that seemed to correspond to a marked change at frame 200 (x-axis), we can begin to see a distinct change from baseline after the image is shown and before the user begins talking, as previously discussed with respect to FIG. 7. The line at frame 200 (x-axis) represents is post-reveal assuming 30 fps video rate.

Referring next to FIG. 9, an analysis hierarchy is shown, and including building upon the collected information to analyze input and collected data. As is shown, a baseline shift analysis is first performed, as described above, at level 910. Next, at level 920, a video content analysis is performed (such as that shown above with respect to FIG. 7, indicating changes in the face of the user. Additionally, at level 930, a prosodic analysis of spoken video of the user may be performed. These inputs may be combined to note gross movement 940, illustrators 945 and manipulators 950. These levels of information may in turn be used to determine affect, for example, such as microexpressions 955, expressions 960 and attitudes 965, resulting in a sentiment analysis. Such a sentiment analysis ultimately allows for the analysis and determination of the sentiment currently held by a user, and may do so in an automated fashion, relying on the automated processes noted above. Finally, a temporal analysis 970 may be performed to determine how the sentiment of the user may change over time.

Figure 10:
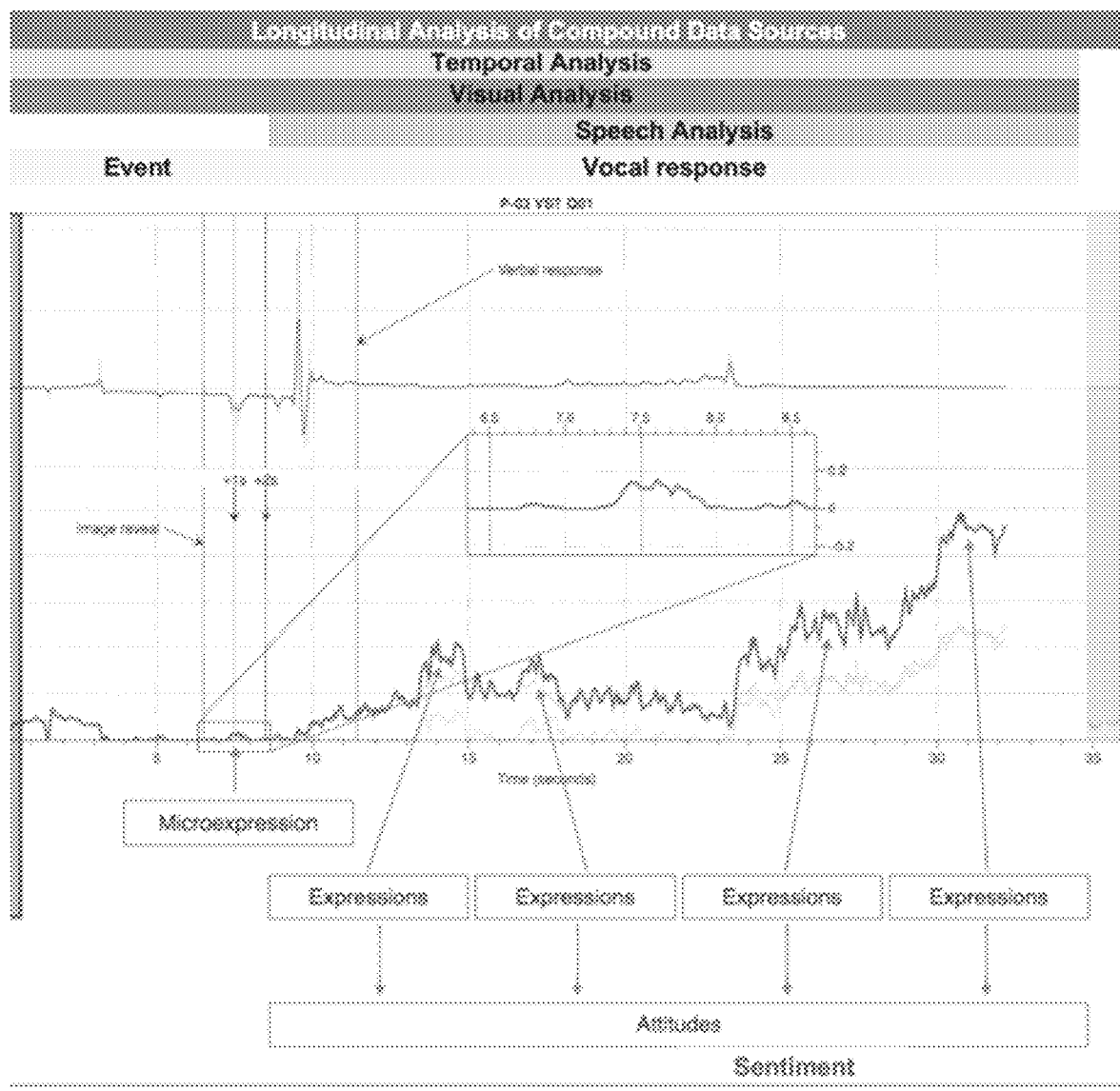
FIG. 10 is a graph representing an exemplary longitudinal analysis of compound data sources.

FIG. 10 depicts graphically the analysis proposed in FIG. 9. As is shown in FIG. 10, longitudinal analysis (looking at data over time, and over multiple instances of data collection across multiple data types) of compound data sources may be used to analyze visual and speech data over time to determine sentiment. As is shown in FIG. 10, an image reveal point corresponding to the point in time at which the system exposes a user to a stimulus, such as an audio or visual stimulus, may allow for the determination of microexpression, as noted above. As time passes, different expressions may be determined, after the period for microexpressions has passed, as also noted above. These microexpressions and expressions may be analyzed to determine attitudes of the user, and ultimately sentiment. By first determining action unit movement, and then facial expression, one is able to further determine attitudes of the users in response to a stimulus (i.e. are they happy when they see a picture of a cute dog), and finally figure out what sentiment they may hold around the subject. These analyses are performed by collecting significant amount of data from subjects with determined baselines, and determining which action unit movements are ultimately indicative of the thoughts, feelings and sentiments of the users. After an additional period of time, it may be beneficial to switch to vocal prosodic analysis in order to determine additional expressions.

Figure 11:
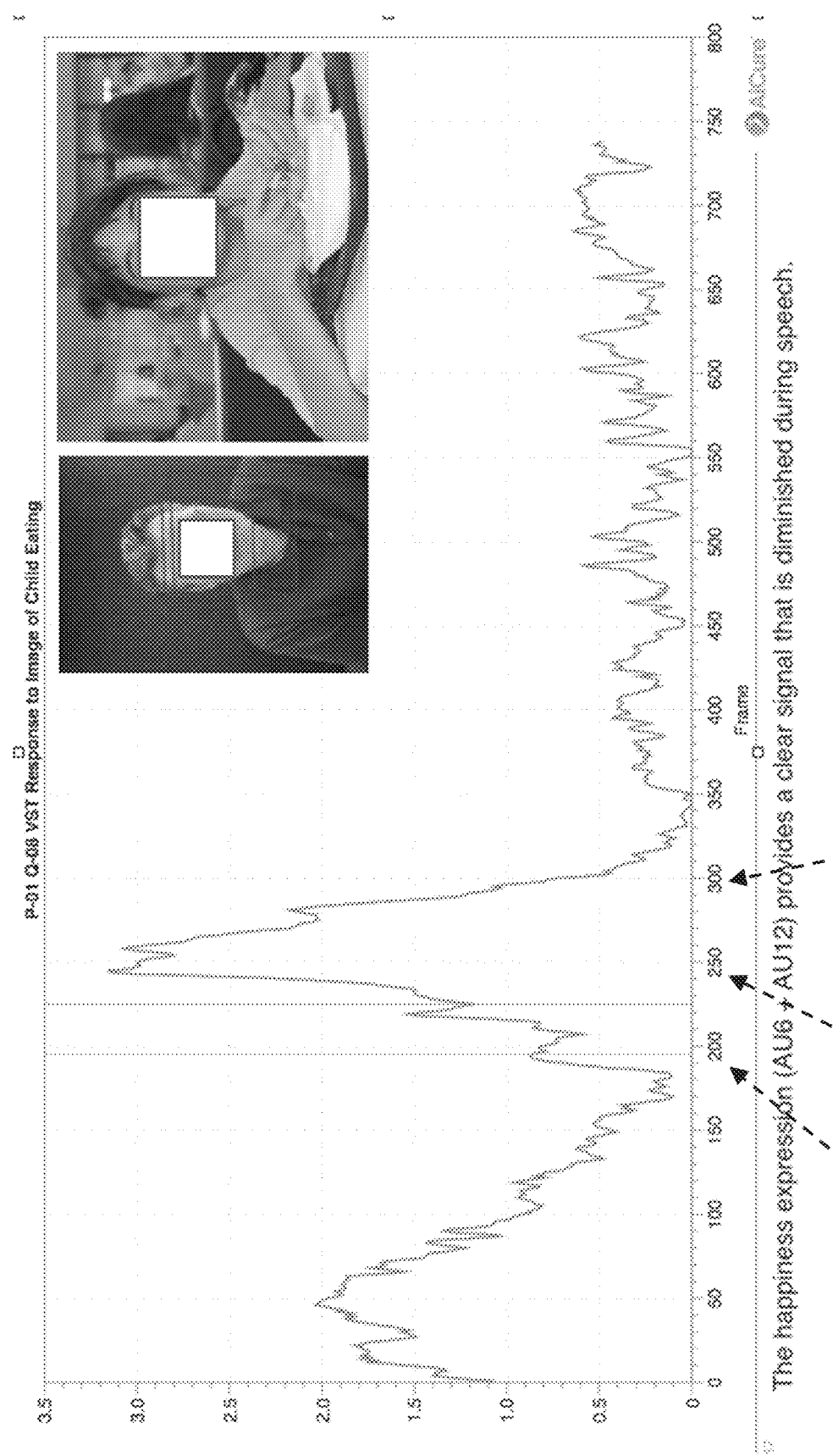
FIG. 11 is a graph depicting an exemplary response where happiness expression is diminished during speech.
Figure 12:
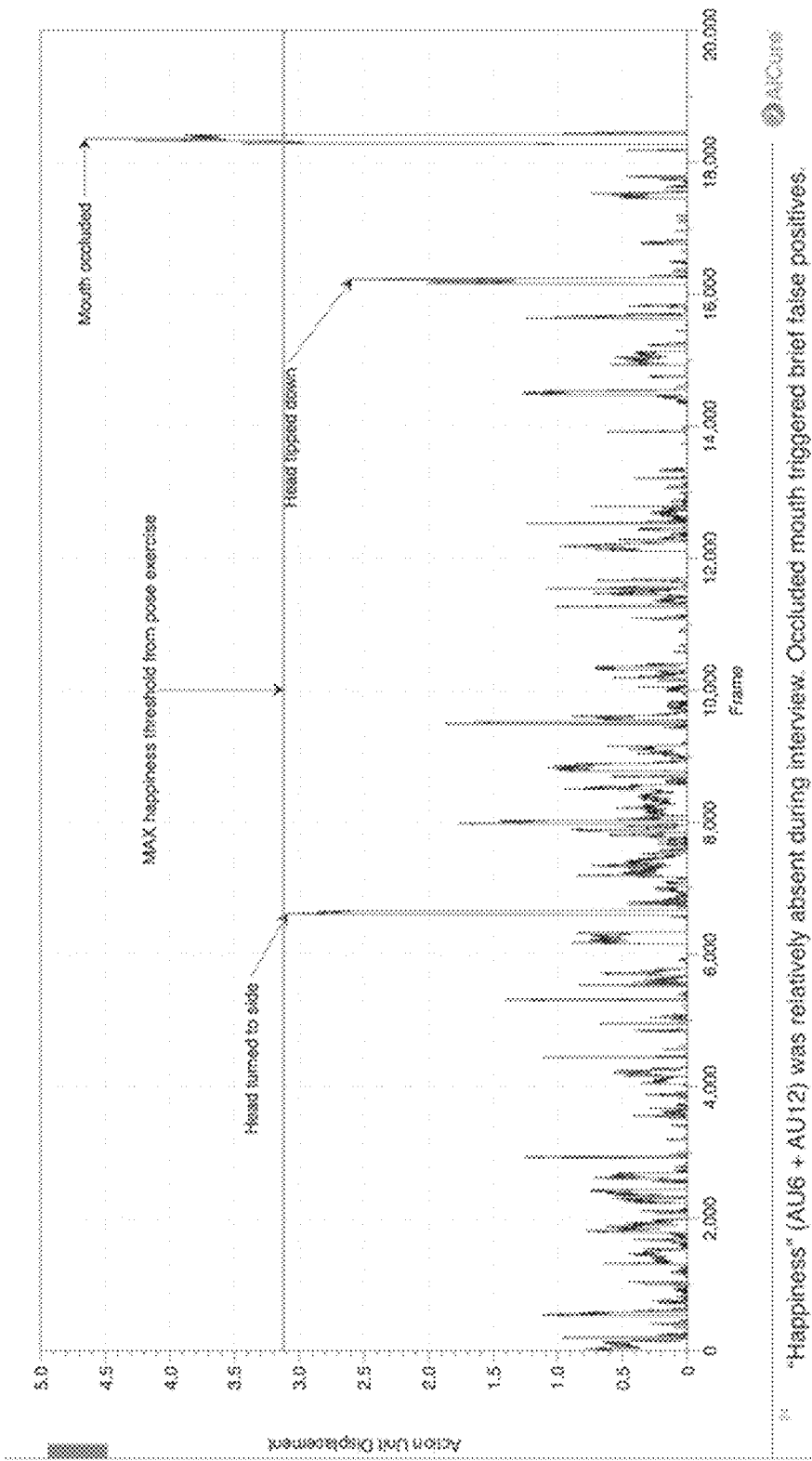
FIG. 12 is a graph depicting an exemplary response where happiness expression is relatively absent during an interview.
Figure 13:
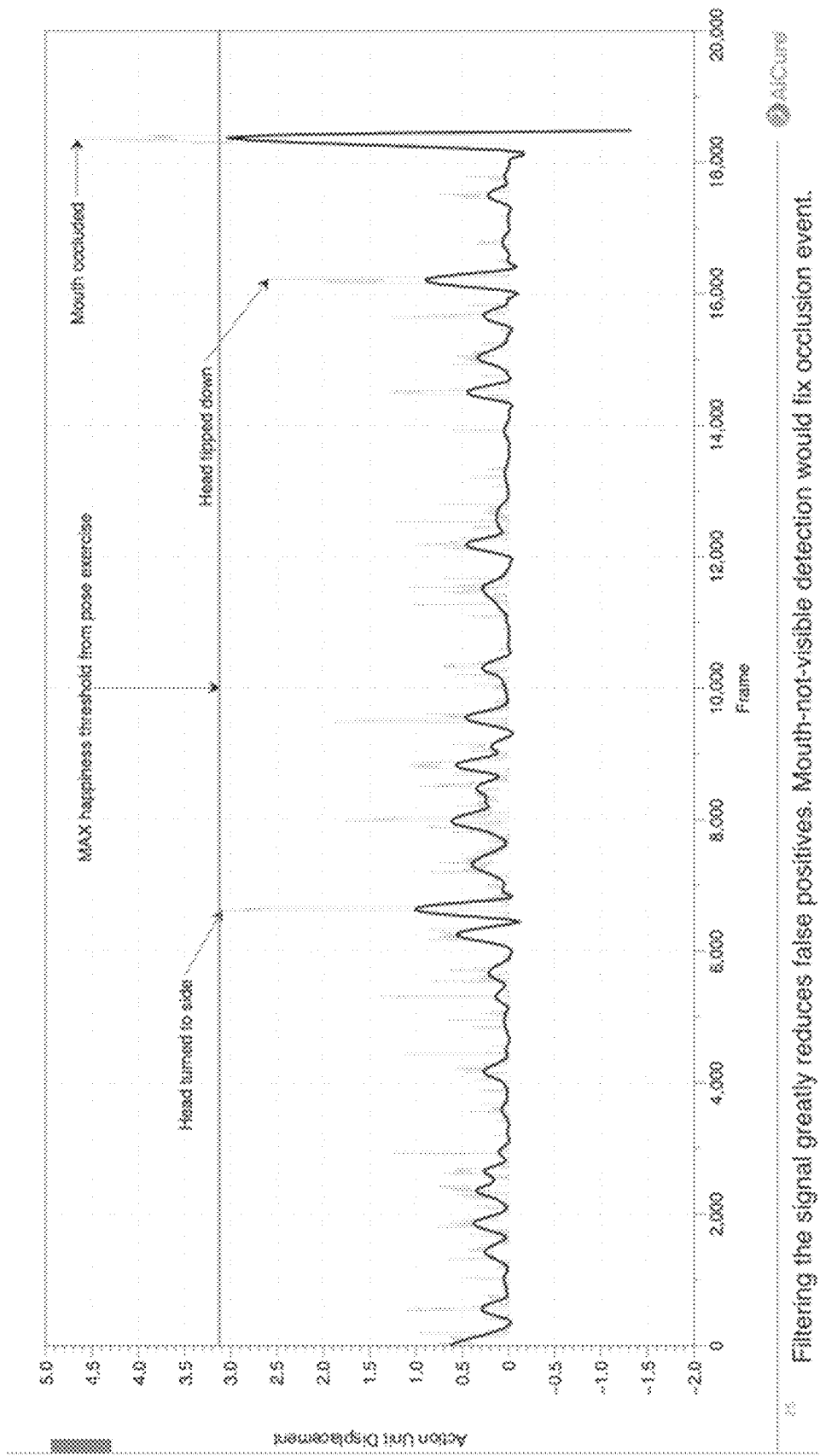
FIG. 13 is a graph depicting a filtered version of the graph of FIG. 12.
Figure 14:
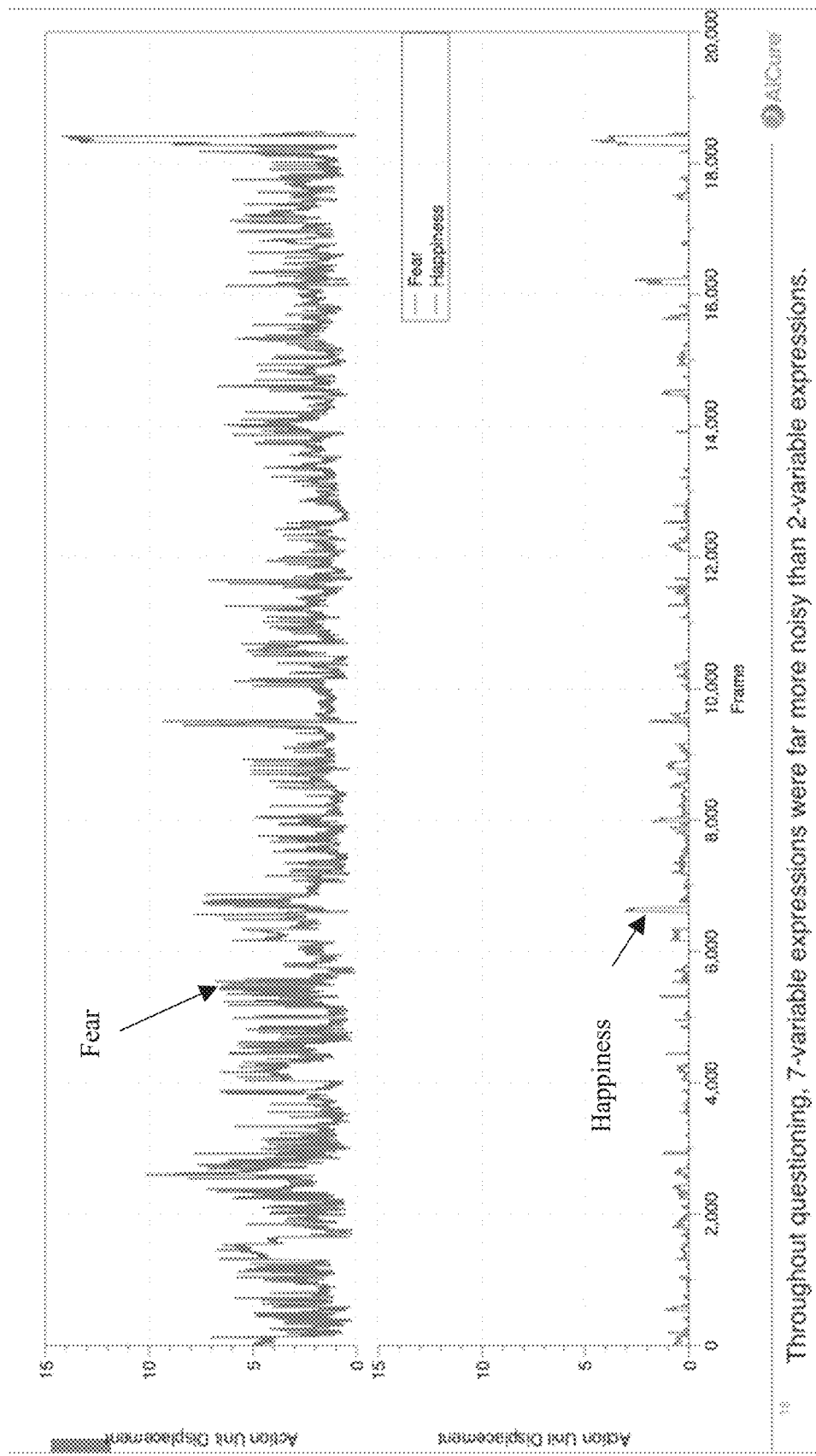
FIG. 14 is a graph depicting an exemplary relative expression between a 7-variable expression and a 2-variable expression.

Referring next to FIG. 11, a graph such as that shown in FIG. 7 is provided, but is limited to the use of action units 6 and 12, as these were determined to be relevant for analysis in this situation. As can be seen, between the vertical lines at 200 and 250 frames lies the microexpression response. At approximately frame 300, speech begins, and the expression (in this case happiness) is greatly repressed. FIG. 12 depicts the same measurement for a greater period of time. Of note are the spikes denoted with action that may have caused them. It is clear that these are not expressions of the user. Therefore, in accordance with some embodiments, and as shown in FIG. 13, it is desirable to filter the waveform to remove such spikes to provide a more consistent waveform related to the actual action unit movement. FIG. 14 depicts that use of multiple action units to determine an action may result in significant noise. FIG. 14 depicts a comparison of the noise between the use of 7 action units and two action units. It is therefore desirable to use fewer action units to make a determination when possible.

Figure 15:
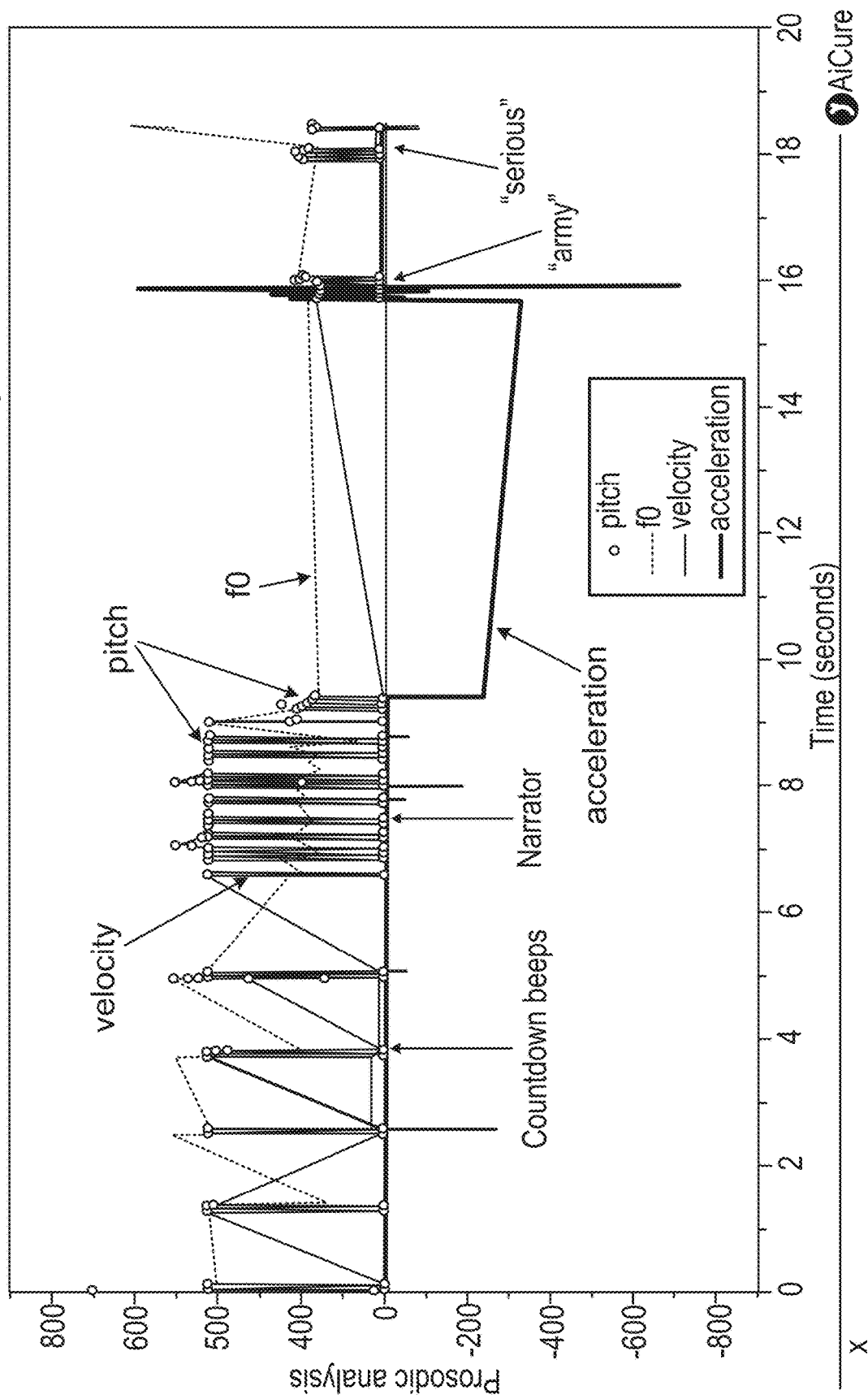
FIG. 15 is a graph depicting an exemplary prosodic analysis in response to a visual stimulation test.

Finally, FIG. 15 depicts the use of prosodic analysis, but combined with the inventive visual analysis. By knowing what the user is looking at, it is possible to provide additional context, thus improving the accuracy of the prosodic readings. For example, when a user is looking at something providing the user happiness, baseline for the prosodic analysis may be altered to give a more accurate response. Prosodic analysis involves analyzing the speech patterns of a person. By determining the speech patterns of an individual, it is possible to measure changes over time of that individual, and to make rudimentary determinations about progression of symptoms or disease. With the presently disclosed systems and techniques, it is possible to correlate prosodic analysis with video analysis of the face of a patient. In some implementations, correlation of movement of action units and prosodic analysis in response to presentation of images or other stimuli to an individual allows for any correlations or lack thereof to be determined. Differences in these correlations between individuals may provide further details of the individual's response and progression of disease. These additional data points allow for a far more complex and extensive analysis, in the manner as described in FIG. 15, which depicts measurement of pitch, velocity and acceleration of the speech pattern of an individual. As is shown, countdown beeps are provided, and after complete, a narrator asking a question, for example, is provided to the individual. The graph then depicts the individual response stating "army" and "serious." The analysis of this responsive speech pattern provides a benchmark for comparison to other individuals, and a baseline for comparison to future analysis of the same user. By the use of prosodic in conjunction with visual analysis data, more specific response patterns and progression of disease and symptoms may be determined.

Therefore, in accordance with the various embodiments of the invention, improved methods and systems are provided for conducting interviews with a user, for analyzing collected video and audio data, and for determining sentiment of the user employing microexpressions and other analysis techniques.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit). Other embedded systems may be employed, such as NVidia® Jetson series or the like.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Processors "configured" to perform one or more of the processes, algorithms, functions, and/or steps disclosed herein include one or more general or special purpose processors as described herein as well as one or more computer and/or machine-readable storage devices on which computer programs for performing the processes are stored.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated. Furthermore, various separate elements may be combined into one or more individual elements to perform the functions described herein.

While visual and audio signals are mainly described in this invention, other data collection techniques may be employed, such as thermal cues or other wavelength analysis of the face or other portions of the body of the user. These alternative data collection techniques may, for example, reveal underlying emotion/response of the patient, such as changes in blood flow, etc. Additionally, visual depth signal measurements may allow for capture subtle facial surface movement correlated with the symptom that may be difficult to detect with typical color images.

Other implementations not specifically described herein are also within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

It should be noted that any of the above-noted inventions may be provided in combination or individually. Elements of different embodiments described herein may be combined to form other embodiments not specifically set forth above. Elements may be left out of the processes, computer programs, etc. described herein without adversely affecting their operation. Furthermore, the system may be employed in mobile devices, computing devices, cloud based storage and processing. Camera images may be acquired by an associated camera, or an independent camera situated at a remote location. Processing may be similarly be provided locally on a mobile device, or a remotely at a cloud-based location, or other remote location. Additionally, such processing and storage locations may be situated at a similar location, or at remote locations.

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

What is claimed is:

1. A system for analysis of changes in symptoms of a patient, the system comprising
    one or more tangible, computer-readable storage media,
    an output device comprising a display, and
    one or more processors, the one or more tangible, computer-readable storage media storing one or more instructions that, when executed by the one or more processors, cause the one or more processors to perform operations comprising:
    providing, to the output device, one or more instructions to perform a first action associated with administration of a medication;
    obtaining first data representing a capture of a patient performing the first action based on the one or more instructions as output by the output device;
    extracting information about movements of the patient from the first data;
    presenting, on the display, an image configured to induce an emotional response in the patient;
    obtaining second data representing capture of the patient performing one or more microexpressions within 250 milliseconds of presentation of the image;
    obtaining additional data comprising one or more of
        demographic information of the patient,
        information of a disease associated with the patient, or
        one or more characteristics of the medication; and
    based on the extracted information about the movements, the one or more microexpressions, and the additional data, determining a medical outcome comprising a progression of the disease in the patient.

2. The system of claim 1, wherein the operations comprise receiving data indicating a potential patient and a proposed medication.

3. The system of claim 2, wherein the potential patient is defined by at least one or more items of demographic information and one or more disease characteristics.

4. The system of claim 3, wherein the operations comprise determining one or more predictions of a reaction of the potential patient to the proposed medication based on the first data and the second data.

5. The system of claim 1, wherein the operations comprise receiving data indicating a proposed patient and a potential medication.

6. The system of claim 5, wherein the potential medication is defined by at least one or more medication characteristics.

7. The system of claim 6, wherein the operations comprise comparing the one or more medication characteristics with medication characteristics of a plurality of other medications stored in a database.

8. The system of claim 7, wherein the operations comprise determining whether prior patients having demographic information similar to that of the proposed patient reacted in a positive manner to other medications sharing at least some of the one or more medication characteristics.

9. The system of claim 8, wherein the operations comprise determining whether the potential medication is predicted to generate a positive outcome for the proposed patient.

10. The system of claim 1, wherein the operations comprise receiving data indicating a proposed disease defined by at least one or more disease characteristics.

11. The system of claim 10, wherein the operations comprise:
comparing the one or more disease characteristics to one or more medication characteristics for one or more medications stored in a database; and
identifying medication characteristics that, when applied to the patient, are determined to result in a positive progression of the disease in the patient.

12. The system of claim 11, wherein the operations comprise identifying, based on the identified medication characteristics, one or more medications that, when applied to the patient, are predicted to result in the positive progression of the disease in the patient.

13. The system of claim 1, wherein the movements of the patient comprise shaking of a hand of the patient.

14. The system of claim 1, wherein the movements of the patient comprise throat movements of the patient.

15. A system for analysis of changes in symptoms of a patient, the system comprising
one or more tangible, computer-readable storage media, an output device comprising a display, and
one or more processors, the one or more tangible, computer-readable storage media storing one or more instructions that, when executed by the one or more processors, cause the one or more processors to perform operations comprising:
obtaining data indicating a current status of a disease in a patient;
based on the current status of the disease, providing, to the output device, a stimulus customized to probe one or more symptoms associated with the disease;
obtaining first data representing capture of the patient performing an action in response to the stimulus;
determining, based on the first data, a change in the one or more symptoms associated with the disease;
obtaining additional data comprising demographic information of the patient and one or more medication characteristics of a medication being administered to the patient;
receiving a request for information;
predicting, in response to the request for information, an outcome of provision of a second medication to a second patient, based on the first data and the additional data; and
returning, to the output device, the predicted outcome.

16. The system of claim 15, wherein the request for information comprises one or more items of demographic information of the second patient and one or more disease characteristics of the second patient, and wherein the predicted outcome comprises one or more predictions of a reaction of the second patient to the second medication.

17. The system of claim 15, wherein the request for information comprises one or more second medication characteristics of the second medication, and wherein predicting the outcome comprises comparing the one or more second medication characteristics with medication characteristics of other medications stored in a database.

18. The system of claim 17, wherein the operations comprise determining whether prior patients having demographic information similar to that of the second patient reacted in a positive manner to other medications sharing at least some of the one or more second medication characteristics.

19. The system of claim 15, wherein the request for information comprises an indication of a proposed disease defined by at least one or more disease characteristics.

20. The system of claim 19, wherein the operations comprise:
comparing the one or more disease characteristics to one or more medication characteristics for one or more medications stored in a database; and
identifying medication characteristics that, when applied to the second patient, are determined to result in a positive progression of the disease in the second patient.

21. The system of claim 20, wherein the operations comprise identifying, based on the identified medication characteristics, one or more medications that, when applied to the second patient, are determined to result in the positive progression of the proposed disease in the second patient.

22. The system of claim 15, wherein the stimulus customized to probe the one or more symptoms comprises display of an image, and
wherein the action performed in response to the stimulus comprises a microexpression performed within 250 milliseconds of display of the image.

23. The system of claim 22, wherein determining the change in the one or more symptoms comprises comparing the microexpression to a visual baseline specific to the patient.

* * * * *